(12) United States Patent
Shikhman et al.

(10) Patent No.: US 10,624,690 B2
(45) Date of Patent: *Apr. 21, 2020

(54) SYSTEMS AND METHODS FOR CONTROLLING USE AND OPERATION OF A FAMILY OF DIFFERENT TREATMENT DEVICES

(71) Applicant: Mederi RF, LLC, Houston, TX (US)

(72) Inventors: Oleg Shikhman, Trumbull, CT (US); William W. Rutan, Norwalk, CT (US)

(73) Assignee: Mederi RF, LLC, Houston, TX (US)

(*) Notice: Subject to any disclaimer, the term of this patent is extended or adjusted under 35 U.S.C. 154(b) by 456 days.

This patent is subject to a terminal disclaimer.

(21) Appl. No.: 15/261,932

(22) Filed: Sep. 10, 2016

(65) Prior Publication Data
US 2016/0374745 A1    Dec. 29, 2016

Related U.S. Application Data

(63) Continuation of application No. 13/651,436, filed on Oct. 14, 2012, now Pat. No. 9,448,681, which is a
(Continued)

(51) Int. Cl.
*A61B 18/12* (2006.01)
*A61B 34/00* (2016.01)
(Continued)

(52) U.S. Cl.
CPC ...... *A61B 18/1206* (2013.01); *A61B 18/1485* (2013.01); *A61B 18/1492* (2013.01);
(Continued)

(58) Field of Classification Search
CPC .. A61N 7/00; A61N 2007/0043; G06F 3/048; G06F 3/04817; G06F 3/04847;
(Continued)

(56) References Cited

U.S. PATENT DOCUMENTS

| 1,798,902 A | 3/1931 | Raney |
| 3,517,128 A | 6/1970 | Hines |

(Continued)

FOREIGN PATENT DOCUMENTS

| CN | 1559351 | 1/2005 |
| CN | 1871609 | 11/2006 |

(Continued)

OTHER PUBLICATIONS

Castell, D.O. Gastroesophageal Reflux Disease: Current Strategies for Patient Management: Arch Fam. Med 5(4): 221-7.
(Continued)

*Primary Examiner* — Michael F Peffley
*Assistant Examiner* — Khadijeh A Vahdat
(74) *Attorney, Agent, or Firm* — Neil D. Gershon

(57) ABSTRACT

A system for controlling a treatment device generates a graphical interface that visually prompts a user in a step-wise fashion to use the treatment device to perform a process of forming a pattern of lesions that extends both circumferentially and axially in different levels in a body region. The graphical interface displays for the user a visual record of the progress of the process from start to finish and guides the user so that so that individual lesions desired within a given level are all formed, and that a given level of lesions is not skipped.

17 Claims, 24 Drawing Sheets

Related U.S. Application Data continuation of application No. 12/924,155, filed on Sep. 22, 2010, now abandoned.

(60) Provisional application No. 61/277,260, filed on Sep. 22, 2009.

(51) Int. Cl.

| | | |
|---|---|---|
| *A61B 18/14* | (2006.01) | |
| *G16H 40/63* | (2018.01) | |
| *G06F 3/048* | (2013.01) | |
| *G06F 3/0481* | (2013.01) | |
| *G06F 3/0484* | (2013.01) | |
| *A61B 34/20* | (2016.01) | |
| *A61B 18/08* | (2006.01) | |
| *A61B 18/18* | (2006.01) | |
| *A61B 18/20* | (2006.01) | |
| *A61B 18/00* | (2006.01) | |
| *A61B 18/02* | (2006.01) | |
| *A61B 18/04* | (2006.01) | |
| *A61N 7/00* | (2006.01) | |

(52) U.S. Cl.
CPC .............. *A61B 34/20* (2016.02); *A61B 34/25* (2016.02); *G06F 3/048* (2013.01); *G06F 3/04817* (2013.01); *G06F 3/04847* (2013.01); *G16H 40/63* (2018.01); *A61B 18/02* (2013.01); *A61B 18/08* (2013.01); *A61B 18/1477* (2013.01); *A61B 18/18* (2013.01); *A61B 18/1815* (2013.01); *A61B 18/20* (2013.01); *A61B 2018/00553* (2013.01); *A61B 2018/0212* (2013.01); *A61B 2018/044* (2013.01); *A61B 2018/1425* (2013.01); *A61B 2018/1807* (2013.01); *A61B 2018/1861* (2013.01); *A61B 2034/2065* (2016.02); *A61B 2034/252* (2016.02); *A61B 2034/254* (2016.02); *A61B 2218/002* (2013.01); *A61B 2218/007* (2013.01); *A61N 7/00* (2013.01); *A61N 2007/0043* (2013.01)

(58) Field of Classification Search
CPC ......... G06F 40/63; A61B 18/02; A61B 18/08; A61B 18/12; A61B 18/1206; A61B 18/1266; A61B 18/14; A61B 18/1442; A61B 18/1445; A61B 18/1448; A61B 18/1477; A61B 18/1485; A61B 18/1492; A61B 18/18; A61B 18/1815; A61B 18/20; A61B 2018/00533; A61B 2018/0212; A61B 2018/044; A61B 2018/1425; A61B 2018/1807; A61B 2018/1861; A61B 2218/002; A61B 2218/007; A61B 34/20; A61B 34/25; A61B 2034/2065; A61B 2034/252; A61B 2034/254
USPC ..................................................... 606/41–50
See application file for complete search history.

(56) References Cited

U.S. PATENT DOCUMENTS

| | | |
|---|---|---|
| 3,901,241 A | 8/1975 | Allen, Jr. |
| 4,011,872 A | 3/1977 | Komiya |
| 4,196,724 A | 4/1980 | Wirt et al. |
| 4,411,266 A | 10/1983 | Cosman |
| 4,423,812 A | 1/1984 | Sato |
| 4,532,924 A | 8/1985 | Auth et al. |
| 4,565,200 A | 1/1986 | Cosman |
| 4,705,041 A | 11/1987 | Kim |
| 4,858,615 A | 8/1989 | Meinema |
| 4,901,737 A | 2/1990 | Toone |
| 4,906,203 A | 3/1990 | Margrave et al. |
| 4,907,589 A | 3/1990 | Cosman |
| 4,943,290 A | 7/1990 | Rexroth et al. |
| 4,947,842 A | 8/1990 | Marchosky et al. |
| 4,955,377 A | 9/1990 | Lennox et al. |
| 4,966,597 A | 10/1990 | Cosman |
| 4,976,711 A | 12/1990 | Parins et al. |
| 4,998,933 A | 3/1991 | Eggers et al. |
| 5,019,075 A | 5/1991 | Spears et al. |
| 5,035,696 A | 7/1991 | Rydell |
| 5,046,512 A | 9/1991 | Murchie |
| 5,047,028 A | 9/1991 | Qian |
| 5,057,107 A | 10/1991 | Parins et al. |
| 5,078,717 A | 1/1992 | Parins et al. |
| 5,083,565 A | 1/1992 | Parins |
| 5,084,044 A | 1/1992 | Quint |
| 5,088,979 A | 2/1992 | Filipi et al. |
| 5,094,233 A | 3/1992 | Brennan |
| 5,100,423 A | 3/1992 | Fearnot |
| 5,106,360 A | 4/1992 | Ishiwara et al. |
| 5,114,423 A | 5/1992 | Kasprzyk et al. |
| 5,122,137 A | 6/1992 | Lennox |
| 5,125,928 A | 6/1992 | Parins et al. |
| 5,156,151 A | 10/1992 | Imran |
| 5,190,541 A | 3/1993 | Abele et al. |
| 5,197,963 A | 3/1993 | Parins |
| 5,197,964 A | 3/1993 | Parins |
| 5,205,287 A | 4/1993 | Erbel et al. |
| 5,215,103 A | 6/1993 | Desai |
| 5,232,444 A | 8/1993 | Just et al. |
| 5,233,515 A | 8/1993 | Cosman |
| 5,236,413 A | 8/1993 | Fiering |
| 5,242,441 A | 9/1993 | Avitall |
| 5,254,126 A | 10/1993 | Filipi et al. |
| 5,256,138 A | 10/1993 | Vurek et al. |
| 5,257,451 A | 11/1993 | Edwards et al. |
| 5,263,493 A | 11/1993 | Avitall |
| 5,275,162 A | 1/1994 | Edwards et al. |
| 5,275,608 A | 1/1994 | Forman et al. |
| 5,275,610 A | 1/1994 | Eberbach |
| 5,277,201 A | 1/1994 | Stern |
| 5,281,216 A | 1/1994 | Klicek |
| 5,281,217 A | 1/1994 | Edwards et al. |
| 5,281,218 A | 1/1994 | Imran |
| 5,290,286 A | 3/1994 | Parins |
| 5,292,321 A | 3/1994 | Lee |
| 5,293,869 A | 3/1994 | Edwards et al. |
| 5,305,696 A | 4/1994 | Mendenhall |
| 5,309,910 A | 5/1994 | Edwards et al. |
| 5,313,943 A | 5/1994 | Houser et al. |
| 5,314,466 A | 5/1994 | Stern et al. |
| 5,316,020 A | 5/1994 | Truffer |
| 5,324,284 A | 6/1994 | Imran |
| 5,328,467 A | 7/1994 | Edwards et al. |
| 5,330,518 A | 7/1994 | Neilson et al. |
| 5,334,193 A | 8/1994 | Nardella |
| 5,334,196 A | 8/1994 | Scott et al. |
| 5,336,222 A | 8/1994 | Durgin, Jr. et al. |
| 5,345,936 A | 9/1994 | Pomeranz et al. |
| 5,348,554 A | 9/1994 | Imran et al. |
| 5,363,347 A | 11/1994 | Nguyen |
| 5,363,861 A | 11/1994 | Edwards et al. |
| 5,365,926 A | 11/1994 | Desai |
| 5,365,945 A | 11/1994 | Halstrom |
| 5,366,490 A | 11/1994 | Edwards et al. |
| 5,368,557 A | 11/1994 | Nita et al. |
| 5,368,592 A | 11/1994 | Stern et al. |
| 5,370,675 A | 12/1994 | Edwards et al. |
| 5,370,678 A | 12/1994 | Edwards et al. |
| 5,383,874 A | 1/1995 | Jackson et al. |
| 5,383,876 A | 1/1995 | Nardella |
| 5,383,917 A | 1/1995 | Desai et al. |
| 5,385,544 A | 1/1995 | Edwards et al. |
| 5,385,917 A | 1/1995 | Ueno et al. |
| 5,397,339 A | 3/1995 | Desai |
| 5,398,683 A | 3/1995 | Edwards et al. |
| 5,401,272 A | 3/1995 | Perkins |

(56) References Cited

U.S. PATENT DOCUMENTS

| | | |
|---|---|---|
| 5,403,311 A | 4/1995 | Abele et al. |
| 5,409,453 A | 4/1995 | Lundquist et al. |
| 5,409,483 A | 4/1995 | Campbell et al. |
| 5,415,657 A | 5/1995 | Taymor-Luria |
| 5,421,819 A | 6/1995 | Edwards et al. |
| 5,423,808 A | 6/1995 | Edwards et al. |
| 5,423,811 A | 6/1995 | Ellman et al. |
| 5,423,812 A | 6/1995 | Ellman et al. |
| 5,433,198 A | 7/1995 | Desai |
| 5,433,739 A | 7/1995 | Sluijter et al. |
| 5,435,805 A | 7/1995 | Edwards |
| 5,441,499 A | 8/1995 | Fritzsch |
| 5,443,463 A | 8/1995 | Stern et al. |
| 5,443,470 A | 8/1995 | Stern et al. |
| 5,454,782 A | 10/1995 | Perkins |
| 5,456,662 A | 10/1995 | Edwards et al. |
| 5,456,682 A | 10/1995 | Edwards et al. |
| 5,458,596 A | 10/1995 | Lax et al. |
| 5,458,597 A | 10/1995 | Edwards et al. |
| 5,465,717 A | 11/1995 | Imran et al. |
| 5,470,308 A | 11/1995 | Edwards et al. |
| 5,471,982 A | 12/1995 | Edwards et al. |
| 5,472,441 A | 12/1995 | Edwards et al. |
| 5,484,400 A | 1/1996 | Edwards et al. |
| 5,486,161 A | 1/1996 | Lax et al. |
| 5,490,984 A | 2/1996 | Freed |
| 5,496,271 A | 3/1996 | Burton et al. |
| 5,496,311 A | 3/1996 | Abele et al. |
| 5,500,012 A | 3/1996 | Brucker et al. |
| 5,505,728 A | 4/1996 | Ellman et al. |
| 5,505,730 A | 4/1996 | Edwards |
| 5,507,743 A | 4/1996 | Edwards et al. |
| 5,509,419 A | 4/1996 | Edwards et al. |
| 5,514,130 A | 5/1996 | Baker |
| 5,514,131 A | 5/1996 | Edwards et al. |
| 5,520,684 A | 5/1996 | Imran |
| 5,531,676 A | 7/1996 | Edwards et al. |
| 5,531,677 A | 7/1996 | Lundquist et al. |
| 5,536,240 A | 7/1996 | Edwards et al. |
| 5,536,267 A | 7/1996 | Edwards et al. |
| 5,540,655 A | 7/1996 | Edwards et al. |
| 5,549,644 A | 8/1996 | Lundquist et al. |
| 5,554,110 A | 9/1996 | Edwards et al. |
| 5,556,377 A | 9/1996 | Rosen et al. |
| 5,558,672 A | 9/1996 | Edwards et al. |
| 5,558,673 A | 9/1996 | Edwards et al. |
| 5,562,720 A | 10/1996 | Stern et al. |
| 5,571,116 A | 11/1996 | Bolanos et al. |
| 5,578,007 A | 11/1996 | Imran |
| 5,588,432 A | 12/1996 | Crowley |
| 5,588,960 A | 12/1996 | Edwards et al. |
| 5,599,345 A | 2/1997 | Edwards et al. |
| 5,609,151 A | 3/1997 | Mulier et al. |
| 5,624,439 A | 4/1997 | Edwards et al. |
| 5,651,780 A | 7/1997 | Jackson et al. |
| 5,672,153 A | 9/1997 | Lax et al. |
| 5,672,174 A | 9/1997 | Gough et al. |
| 5,676,674 A | 10/1997 | Bolanos et al. |
| 5,688,266 A | 11/1997 | Edwards et al. |
| 5,688,490 A | 11/1997 | Tournier et al. |
| 5,702,438 A | 12/1997 | Avitall |
| 5,709,224 A | 1/1998 | Behl et al. |
| 5,732,698 A | 3/1998 | Swanson et al. |
| 5,733,319 A | 3/1998 | Neilson et al. |
| 5,738,096 A | 4/1998 | Ben-Haim |
| 5,742,718 A | 4/1998 | Harman et al. |
| 5,743,903 A | 4/1998 | Stern et al. |
| 5,759,158 A | 6/1998 | Swanson |
| 5,769,847 A | 6/1998 | Panescu et al. |
| 5,800,482 A | 9/1998 | Pomeranz et al. |
| 5,827,276 A | 10/1998 | Le Veen et al. |
| 5,830,213 A | 11/1998 | Panescu et al. |
| 5,836,874 A | 11/1998 | Swanson et al. |
| 5,848,969 A | 12/1998 | Panescu et al. |
| 5,855,576 A | 1/1999 | Le Veen et al. |
| 5,860,974 A | 1/1999 | Abele |
| 5,871,469 A | 2/1999 | Eggers et al. |
| 5,871,481 A | 2/1999 | Kannenberg et al. |
| 5,871,483 A | 2/1999 | Jackson et al. |
| 5,876,336 A | 3/1999 | Swanson et al. |
| 5,891,030 A | 4/1999 | Johnson et al. |
| 5,916,163 A | 6/1999 | Panescu et al. |
| 5,931,835 A | 8/1999 | Mackey |
| 5,957,961 A | 9/1999 | Maguire et al. |
| 6,004,269 A | 12/1999 | Crowley et al. |
| 6,006,755 A | 12/1999 | Edwards |
| 6,009,877 A | 1/2000 | Edwards |
| 6,014,581 A | 1/2000 | Whayne et al. |
| 6,023,638 A | 2/2000 | Swanson |
| 6,044,846 A | 4/2000 | Edwards |
| 6,056,744 A | 5/2000 | Edwards |
| 6,073,052 A | 6/2000 | Zelickson et al. |
| 6,092,528 A | 7/2000 | Edwards |
| 6,106,460 A | 8/2000 | Panescu et al. |
| 6,165,169 A | 12/2000 | Panescu et al. |
| 6,197,022 B1 | 3/2001 | Baker |
| 6,231,569 B1 | 5/2001 | Bek et al. |
| 6,235,022 B1 | 5/2001 | Hallock et al. |
| 6,241,725 B1 | 6/2001 | Cosman |
| 6,226,551 B1 | 7/2001 | Osadchy et al. |
| 6,254,598 B1 | 7/2001 | Edwards et al. |
| 6,273,886 B1 | 8/2001 | Edwards et al. |
| 6,355,031 B1 | 3/2002 | Edwards et al. |
| 6,358,245 B1 | 3/2002 | Edwards et al. |
| 6,387,092 B1 | 5/2002 | Burnside et al. |
| 6,389,311 B1 | 5/2002 | Whayne et al. |
| 6,391,024 B1 | 5/2002 | Sun et al. |
| 6,402,744 B2 | 6/2002 | Edwards et al. |
| 6,409,723 B1 | 6/2002 | Edwards |
| 6,464,689 B1 | 10/2002 | Qin et al. |
| 6,464,697 B1 | 10/2002 | Edwards et al. |
| 6,478,793 B1 | 11/2002 | Cosman et al. |
| 6,544,226 B1 | 4/2003 | Gaiser et al. |
| 6,547,776 B1 | 4/2003 | Gaiser et al. |
| 6,575,969 B1 | 6/2003 | Rittman et al. |
| 6,589,238 B2 | 7/2003 | Edwards et al. |
| 6,645,201 B1 | 11/2003 | Utley et al. |
| 6,695,806 B2 | 2/2004 | Gelfand et al. |
| 6,699,243 B2 | 3/2004 | West et al. |
| 6,733,495 B1 | 5/2004 | Bek et al. |
| 6,783,523 B2 | 8/2004 | Qin et al. |
| 6,790,207 B2 | 9/2004 | Utley et al. |
| 6,802,841 B2 | 10/2004 | Utley et al. |
| 6,827,713 B2 | 12/2004 | Bek et al. |
| 6,835,202 B2 | 12/2004 | Harth et al. |
| 7,258,688 B1 | 8/2007 | Shah et al. |
| 2002/0013581 A1* | 1/2002 | Edwards ............... A61B 18/12 606/41 |
| 2002/0151871 A1 | 10/2002 | Gaiser et al. |
| 2002/0162555 A1 | 11/2002 | West et al. |
| 2002/0193787 A1 | 12/2002 | Qin et al. |
| 2002/0198519 A1 | 12/2002 | Qin et al. |
| 2003/0078490 A1 | 4/2003 | Damasco et al. |
| 2003/0109778 A1 | 6/2003 | Rashidi |
| 2004/0089313 A1 | 5/2004 | Utley et al. |
| 2004/0133189 A1 | 7/2004 | Sakurai |
| 2005/0143632 A1 | 6/2005 | Elaz et al. |
| 2005/0187546 A1 | 8/2005 | Bek et al. |
| 2006/0046031 A1 | 3/2006 | Janevski |
| 2008/0097422 A1 | 4/2008 | Edwards et al. |
| 2008/0154253 A1 | 6/2008 | Damasco et al. |
| 2009/0171184 A1 | 7/2009 | Jenkins et al. |
| 2010/0130836 A1 | 5/2010 | Malchano et al. |
| 2010/0204694 A1 | 8/2010 | Mehta et al. |
| 2011/0257646 A1 | 10/2011 | Utley et al. |
| 2013/0102889 A1 | 4/2013 | Southard et al. |
| 2013/0237979 A1 | 9/2013 | Shikhman et al. |

FOREIGN PATENT DOCUMENTS

| | | |
|---|---|---|
| CN | 201710641 | 1/2011 |
| DE | 4303882 | 2/1995 |

(56) References Cited

FOREIGN PATENT DOCUMENTS

| | | |
|---|---|---|
| DE | 3838840 | 2/1997 |
| EP | 0139607 | 5/1985 |
| EP | 0608609 | 8/1994 |
| EP | 0765813 | 4/1997 |
| JP | 2004-105502 | 4/2004 |
| WO | WO-91/01773 | 2/1991 |
| WO | WO-92/10142 | 6/1992 |
| WO | WO-93/08755 | 5/1993 |
| WO | WO-94/10925 | 5/1994 |
| WO | WO-94/21165 | 9/1994 |
| WO | WO-94/21178 | 9/1994 |
| WO | WO-94/22366 | 10/1994 |
| WO | WO-94/26178 | 11/1994 |
| WO | WO-95/15875 | 7/1995 |
| WO | WO-95/19142 | 7/1995 |
| WO | WO-95/25472 | 9/1995 |
| WO | WO-96/00042 | 1/1996 |
| WO | WO-96/16606 | 1/1996 |
| WO | WO-96/29946 | 1/1996 |
| WO | WO-96/36860 | 11/1996 |
| WO | WO-96/41654 | 12/1996 |
| WO | WO-97/06857 | 2/1997 |
| WO | WO 97/25011 | 7/1997 |
| WO | WO-97/32532 | 9/1997 |
| WO | WO-97/43971 | 11/1997 |
| WO | WO-99/17671 | 4/1999 |
| WO | WO-00/66052 | 11/2000 |
| WO | WO-01/017452 | 3/2001 |
| WO | WO-01/024721 | 4/2001 |
| WO | WO-04/107989 | 12/2004 |
| WO | WO-11/037621 | 10/2011 |
| WO | WO 2013/055707 | 4/2013 |

OTHER PUBLICATIONS

Castell, D.O. Gastroesophageal Reflux Disease: Current Strategies for Patient Management: Arch Fam. Med 5(4): 221-7. Apr. 5, 1996 Abstract Only.
Dallemagne, B. et al., "Laparoscopic Nissen Fundoplication: Preliminary," Surgical Laparoscopy & Endoscopy. 1991 1(3): 138-43.
Kelly, KA et al., "Duodenal-gastric reflux and slowed gastric emptying by electrical pacing of the canine duodenal pacesetter potential," Gastroenterology. 1997.72 (3): 429-33.
Reynolds, J.C. "Influence of pathophysiology, severity, and cost on the medical management of gastroesophageal reflux disease," Am J. Health-Syst Pharm. 53 (22 suppl 3): S5-12.
Urschel, J.D. "Complications of Antireflux Surgery," Am J. Surg. 1993. 166 (1): 68-70.
Kaneko, et al., Physiological Laryngeal Pacemaker, May 1985, Trans Am Soc. Artif. Intern Organs, vol. XXXI, pp. 293-296.
Mugica, et al. Direct Diaphragm Stimulation, Jan. 1987 PACE, vol. 10, pp. 252-256.
Mugica, et al., Neurostimulation: An Overview, Chapter 21, Preliminary Test of a Muscular Diaphragm Pacing System on Human Patients. 1985. pp. 3. 263-279.
Reynolds, J.C. "Influence of pathophysiology, severity, and cost on the medical management of gastroesophageal reflux disease," Am J. Health-Syst Pharm. 53 (22 suppl 3): S5-12. Nov. 15, 1996 Abstract Only.
Rice, et al., Endoscopic Paranasal Sinus Surgery, Chapter 5, Endoscopic Paranasal Sinus Surgery, The Technique of Messerklinger, Raven Press, 1988, pp. 75-104.
Rice, et al., Endoscopic Paranasal Sinus Surgery, Chapter 6, Functional Endoscopic Paranasal Sinus Surgery, The Technique of Wigand, Raven Press, 1988, pp. 105-125.
Karlstrom, L.H., et al., Exotopic jejunal pacemakers and enterogastric reflux after Roux gastrectomy; Effect of intestinal pacing. Surgery 1989. 106 (3): 486-495.
Hinder; R.A., et al. "The Technique of Laparoscopic Nissen Fundoplication," Surgical Laparoscopy & Endoscopy. 1992. 2 (3): 265-272.

* cited by examiner

SYSTEMS AND METHODS FOR CONTROLLING USE AND OPERATION OF A FAMILY OF DIFFERENT TREATMENT DEVICES

RELATED APPLICATIONS

This application is a continuation of application Ser. No. 13/651,436, filed Oct. 14, 2012, now U.S. Pat. No. 9,448,681, which is a continuation of application Ser. No. 12/924,155, filed Sep. 22, 2010, now abandoned, which claims priority from provisional application Ser. No. 61/277,260 filed Sep. 22, 2009. The entire contents of each of these applications are incorporated herein by reference.

FIELD OF THE INVENTION

In a general sense, the invention is directed to systems and methods for treating interior tissue regions of the body. More specifically, the invention is directed to systems and methods for treating dysfunction in body sphincters and adjoining tissue.

BACKGROUND OF THE INVENTION

The gastrointestinal (GI) tract, also called the alimentary canal, is a long tube through which food is taken into the body and digested. The alimentary canal begins at the mouth, and includes the pharynx, esophagus, stomach, small and large intestines, and rectum. In human beings, this passage is about 30 feet (9 meters) long.

Small, ring-like muscles, called sphincters, surround portions of the alimentary canal. In a healthy person, these muscles contract or tighten in a coordinated fashion during eating and the ensuing digestive process, to temporarily close off one region of the alimentary canal from another region of the alimentary canal.

For example, a muscular ring called the lower esophageal sphincter (or LES) surrounds the opening between the esophagus and the stomach. Normally, the lower esophageal sphincter maintains a high-pressure zone between fifteen and thirty mm Hg above intragastric pressures inside the stomach.

In the rectum, two muscular rings, called the internal and external sphincter muscles, normally keep fecal material from leaving the anal canal. The external sphincter muscle is a voluntary muscle, and the internal sphincter muscle is an involuntary muscle. Together, by voluntary and involuntary action, these muscles normally contract to keep fecal material in the anal canal.

Dysfunction of a sphincter in the body can lead to internal damage or disease, discomfort, or otherwise adversely affect the quality of life. For example, if the lower esophageal sphincter fails to function properly, stomach acid may rise back into the esophagus. Heartburn or other disease symptoms, including damage to the esophagus, can occur. Gastrointestinal reflux disease (GERD) is a common disorder, characterized by spontaneous relaxation of the lower esophageal sphincter.

Damage to the external or internal sphincter muscles in the rectum can cause these sphincters to dysfunction or otherwise lose their tone, such that they can no longer sustain the essential fecal holding action. Fecal incontinence results, as fecal material can descend through the anal canal without warning, stimulating the sudden urge to defecate. The physical effects of fecal incontinence (i.e., the loss of normal control of the bowels and gas, liquid, and solid stool leakage from the rectum at unexpected times) can also cause embarrassment, shame, and a loss of confidence, and can further lead to mental depression.

SUMMARY OF THE INVENTION

One aspect of the invention provides systems and methods for treating body tissue that comprise generating a graphical display for visually prompting a user in a step-wise fashion to use a treatment device to perform a process of forming a pattern of lesions in a body region comprising a plurality of axially spaced lesion levels, each lesion level comprising a plurality of circumferential spaced lesions. The systems and methods include registering the formation of lesions as they are generated in real time, both within and between each circumferentially spaced level, whereby the graphical display displays for the user a visual record of the progress of the process from start to finish and guides the user so that individual lesions desired within a given level are all formed, and that a given level of lesions is not skipped.

In one embodiment, the systems and methods include generating at each lesion level a first stylized graphical image with a number identification of its level, and generating a second stylized graphical image, different from the first stylized graphical image, generated when the formation of lesions at a given level is indicated and further showing the number of lesions to be formed at that level. The systems and methods include changing the second graphical image to a third graphical image, different than the first or second images, including added indicia to reflect the formation of lesions in real time. The systems and methods further include generating, upon forming the desired lesion pattern on the respective lesion level, a fourth graphical image, different than the first, second, and third graphical images, comprising an indicator to indicate that all desired lesions have been formed at the level. The systems and methods further include generating a marker that directs the user to the next lesion level to be treated and that is updated as successive lesion levels are treated.

Further features and advantages of the inventions are set forth in the following Description and Drawings, as well as in the appended claims.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF PREFERRED EMBODIMENTS

This Specification discloses various systems and methods for treating dysfunction of sphincters and adjoining tissue regions in the body. The systems and methods are particularly well suited for treating these dysfunctions in the upper and lower gastrointestinal tract, e.g., gastro-esophageal reflux disease (GERD) affecting the lower esophageal sphincter and adjacent cardia of the stomach, or fecal incontinence affecting the internal and external sphincters of the anal canal. For this reason, the systems and methods will be described in this context. Still, it should be appreciated that the disclosed systems and methods are applicable for use in treating other dysfunctions elsewhere in the body, and dysfunctions that are not necessarily sphincter-related. For example, the various aspects of the invention have application in procedures requiring treatment of hemorrhoids, or urinary incontinence, or restoring compliance to or otherwise tightening interior tissue or muscle regions. The systems and methods that embody features of the invention are also adaptable for use with systems and surgical techniques that catheter-based and not necessarily catheter-based.

I. Overview of the System

Figure 1:
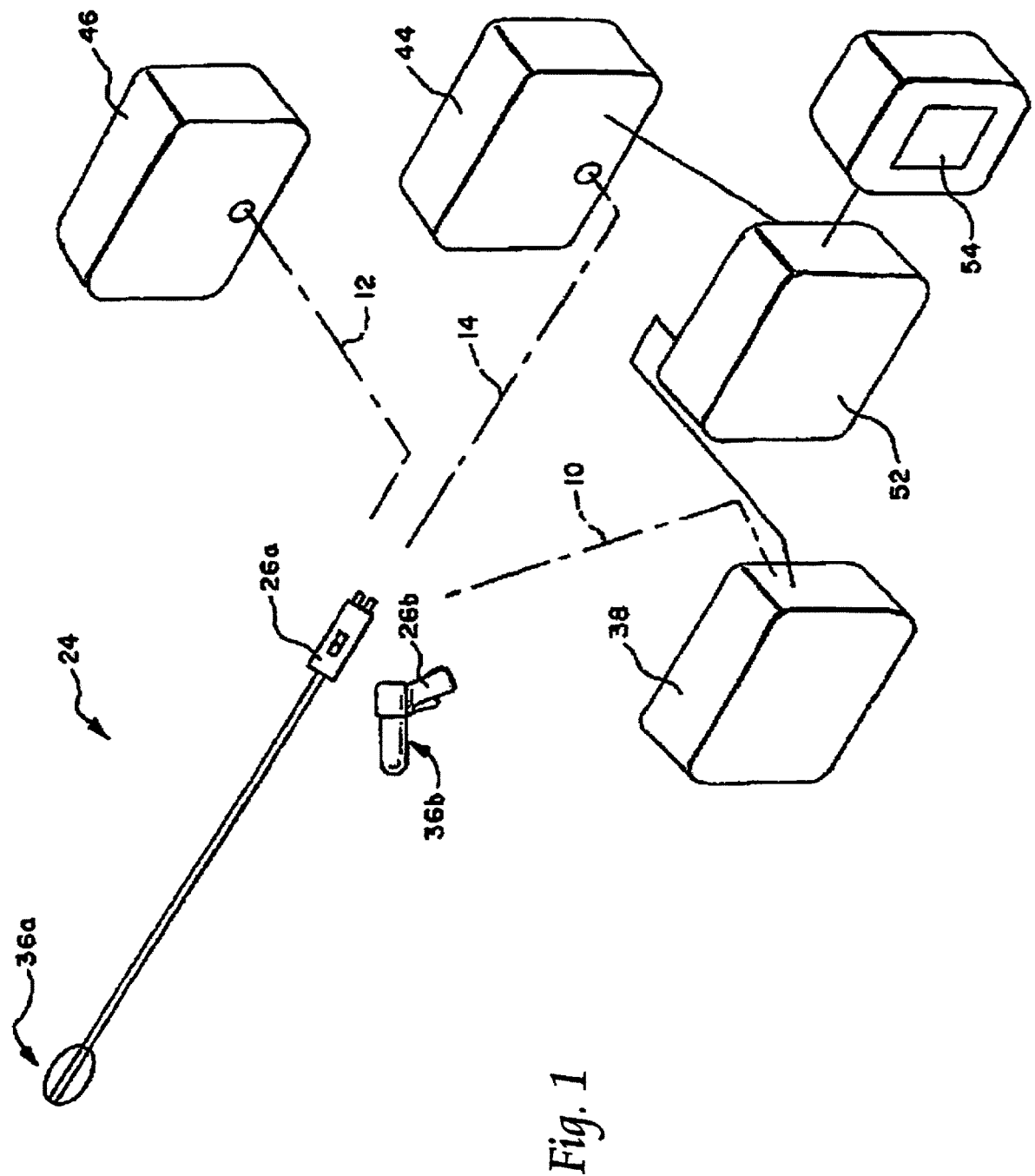
FIG. 1 is a diagrammatic view of a unified system usable in association with a family of different treatment devices for treating body sphincters and adjoining tissue regions in different regions of the body.

FIG. 1 shows a unified system 24 for diagnosing and/or treating dysfunction of sphincters and adjoining tissue in different regions of the body. In the illustrated embodiment, the system 24 is configured to diagnose and treat dysfunction in at least two distinct sphincter regions within the body.

The targeted sphincter regions can vary. In the illustrated embodiment, one region comprises the upper gastro-intestinal tract, e.g., the lower esophageal sphincter and adjacent cardia of the stomach. The second region comprises the lower gastrointestinal tract, e.g., in the intestines, rectum and anal canal.

The system 24 includes a family of treatment devices 26a and 26b. Each device 26a and 26b can be specifically configured according to the physiology and anatomy of the particular sphincter region which it is intended to treat. The details of construction of each device 26a and 26b will be generally described later for purposes of illustration, but are not material to the invention.

Each device 26a/26b carries an operative element 36a and 36b. The operative element 36a and 36b can be differently configured according to the physiology and anatomy of the particular sphincter region which it is intended to treated. Still, if the anatomy and physiology of the two treatment regions are the same or similar enough, the configuration of the operative elements 36a and 36b can be same or essentially the same.

In the illustrated embodiment, the operative elements 36a and 36b function in the system 10 to apply energy in a selective fashion to tissue in or adjoining the targeted sphincter region. The applied energy creates one or more lesions, or a prescribed pattern of lesions, below the surface of the targeted region. The subsurface lesions are desirably formed in a manner that preserves and protects the surface against thermal damage.

Natural healing of the subsurface lesions leads to a physical tightening of the targeted tissue. The subsurface lesions can also result in the interruption of aberrant electrical pathways that may cause spontaneous sphincter relaxation. In any event, the treatment can restore normal closure function to the sphincter region 18.

The system 24 includes a generator 38 to supply the treatment energy to the operative element 36a/36b of the device 26a/26b selected for use. In the illustrated embodiment, the generator 38 supplies radio frequency energy, e.g., having a frequency in the range of about 400 kHz to about 10 mHz. Of course, other forms of energy can be applied, e.g., coherent or incoherent light; heated or cooled fluid; resistive heating; microwave; ultrasound; a tissue ablation fluid; or cryogenic fluid.

A selected device 26a/26b can be individually coupled to the generator 38 via a cable 10 to convey the generated energy to the respective operative element 36a/36b.

The system 24 preferably also includes certain auxiliary processing equipment. In the illustrated embodiment, the processing equipment comprises an external fluid delivery apparatus 44 and an external aspirating apparatus 46.

A selected device 26a/26b can be connected via tubing 12 to the fluid delivery apparatus 44, to convey processing fluid for discharge by or near the operative element 36a/36b. A selected device 26a/26b can also be connected via tubing 14 to the aspirating apparatus 46, to convey aspirated material from or near from the operative element 36a/36b for discharge.

The system 24 also includes a controller 52. The controller 52, which preferably includes a central processing unit (CPU), is linked to the generator 38, the fluid delivery apparatus 44, and the aspirating apparatus 46. Alternatively, the aspirating apparatus 46 can comprise a conventional vacuum source typically present in a physician's suite, which operates continuously, independent of the controller 52.

The controller 52 governs the power levels, cycles, and duration that the radio frequency energy is distributed to the particular operative element 36a/36b, to achieve and maintain power levels appropriate to achieve the desired treatment objectives. In tandem, the controller 52 also desirably governs the delivery of processing fluid and, if desired, the removal of aspirated material.

The controller 52 includes an input/output (I/O) device 54. The I/O device 54 allows the physician to input control and processing variables, to enable the controller to generate appropriate command signals. The I/O device 54 also receives real time processing feedback information from one or more sensors associated with the operative element (as will be described later), for processing by the controller 52, e.g., to govern the application of energy and the delivery of processing fluid.

The I/O device 54 also includes a graphical user interface (GUI), to graphically present processing information to the physician for viewing or analysis. Further details regarding the GUI will be provided later.

II. The Treatment Devices

The structure of the operative element 36 can vary. Various representative embodiments will be described.

A. For Treatment of Upper Gastro-Intestinal Tract

Figure 2:
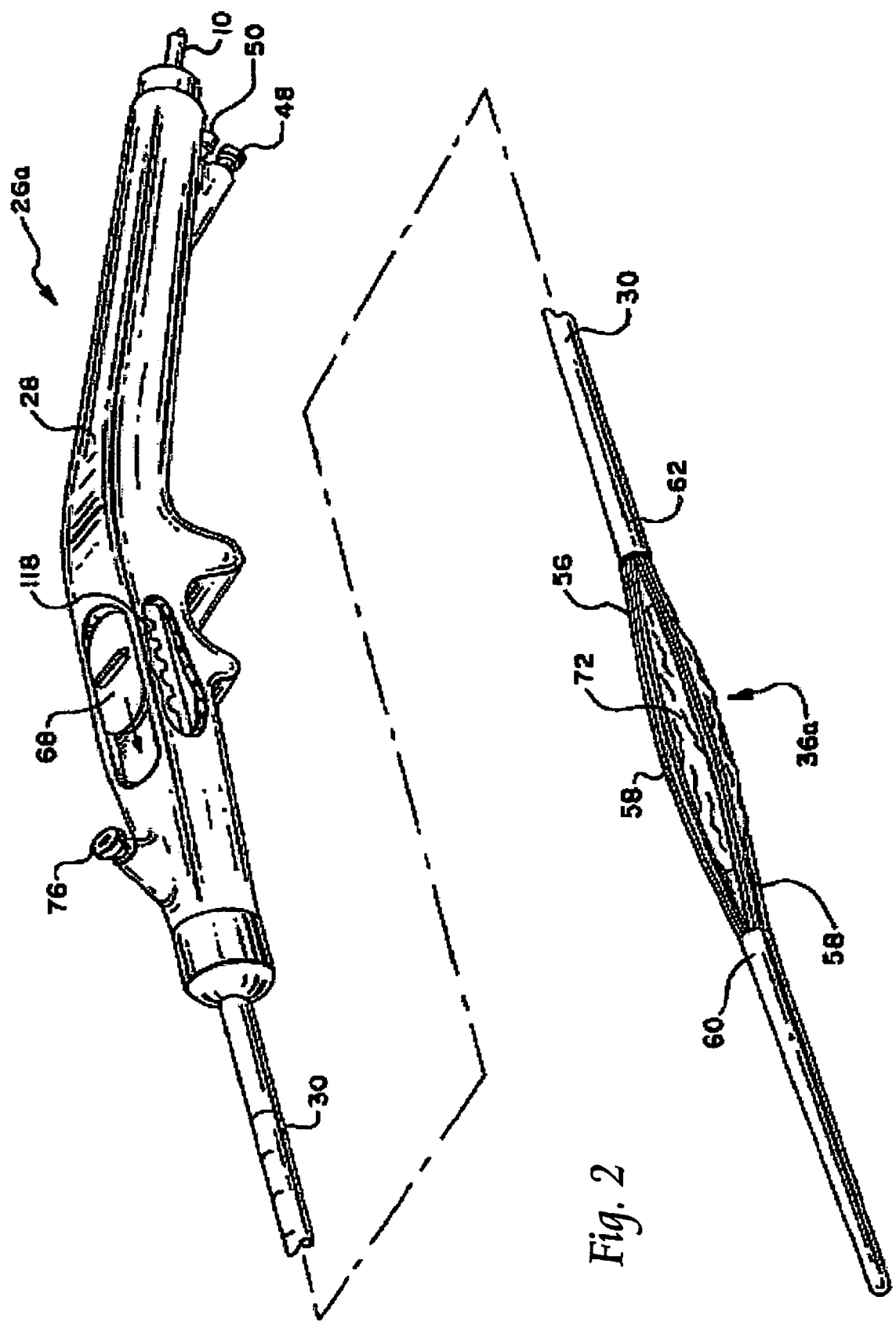
FIG. 2 is a perspective view, with portions broken away, of one type of treatment device usable in association with the system shown in FIG. 1 to treat tissue in the upper gastrointestinal tract, the treatment device having an operative element for contacting tissue shown in a collapsed condition.
Figure 3:
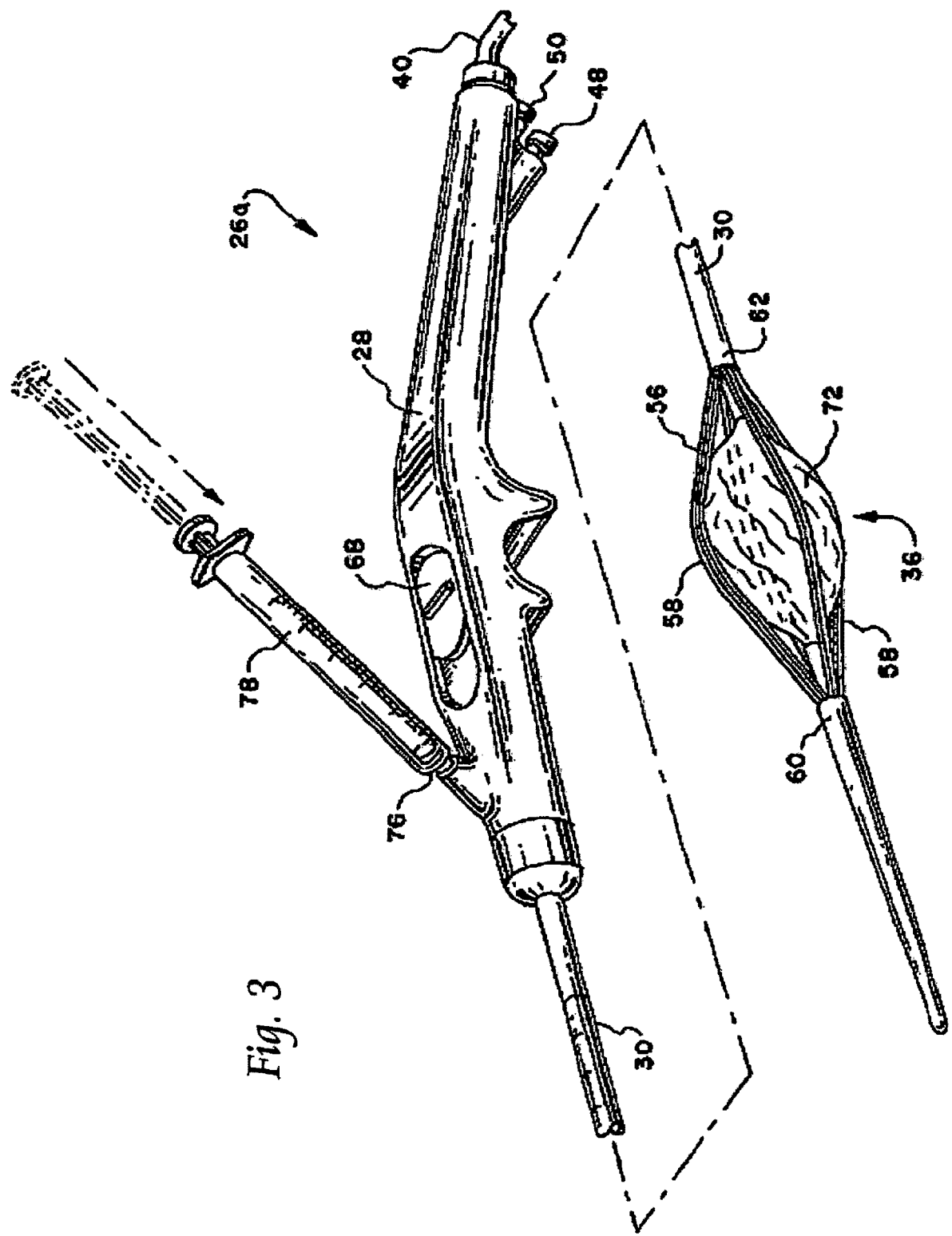
FIG. 3 is a perspective view, with portions broken away, of the device shown in FIG. 2, with the operative element shown in an expanded condition.
Figure 4:
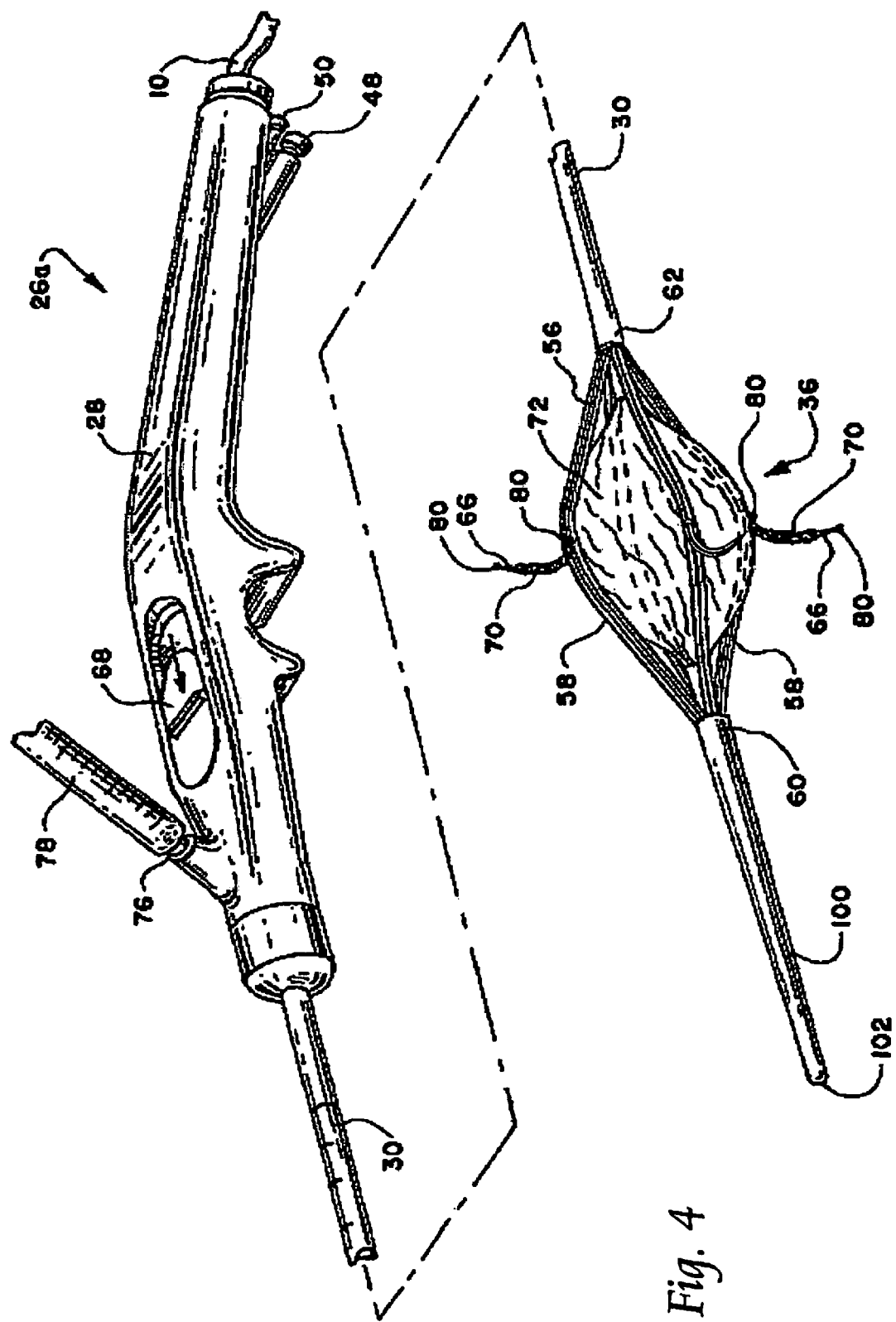
FIG. 4 is a perspective view, with portions broken away, of the device shown in FIG. 2, with the operative element shown in an expanded condition and the electrodes extended for use.

FIGS. 2 to 4 show a catheter-based device 26a for treating sphincter regions in the upper gastro-intestinal tract, and more particularly, the lower esophageal sphincter and adjoining cardia of the stomach to treat GERD. In the embodiment shown, the device 26a includes a flexible catheter tube 30 that carries a handle 28 at its proximal end. The distal end of the catheter tube 30 carries the operative element 36a.

In the illustrated embodiment, the operative element 36a comprises a three-dimensional basket 56. The basket 56 includes one or more spines 58, and typically includes from four to eight spines 58, which are assembled together by a distal hub 60 and a proximal base 62. In the illustrated embodiment, four spines 58 are shown, spaced circumferentially at 90-degree intervals In the illustrated embodiment, an expandable structure 72 comprising a balloon is located within the basket 56. The balloon structure 72 can be made, e.g., from a Polyethylene Terephthalate (PET) material, or a polyamide (non-compliant) material, or a radiation cross-linked polyethylene (semi-compliant) material, or a latex material, or a silicone material, or a C-Flex (highly compliant) material.

The balloon structure 72 presents a normally, generally collapsed condition, as FIG. 2 shows. In this condition, the basket 56 is also normally collapsed about the balloon structure 72, presenting a low profile for deployment into the esophagus.

A catheter tube 30 includes an interior lumen, which communicates with the interior of the balloon structure 72. A fitting 76 (e.g., a syringe-activated check valve) is carried by the handle 28. The fitting 76 communicates with the lumen. The fitting 76 couples the lumen to a syringe 78 (see FIG. 3). The syringe 78 injects fluid under pressure through the lumen into the balloon structure 72, causing its expansion.

Expansion of the balloon structure 72 urges the basket 56 to open and expand (see FIG. 3). The force exerted by the balloon structure 72, when expanded, is sufficient to exert an opening or dilating force upon the tissue surrounding the basket 56 (see FIG. 31).

Each spine 58 carries an electrode 66 (see FIG. 4). Therefore, there are four electrodes circumferentially spaced at 90-degree intervals. In the illustrated embodiment, each electrode 66 is carried within the tubular spine 58 for sliding movement. Each electrode 66 slides from a retracted position, withdrawn in the spine 58 (shown in FIG. 3) and an extended position, extending outward from the spine 58 (see FIG. 4) through a hole in the spine 58. A push-pull lever 68 on the handle 28 is coupled by one or more interior wires to the sliding electrodes 66. The lever 68 controls movement electrodes between the retracted position (by pulling rearward on the lever 68) and the extended position (by pushing forward on the lever 68).

The electrodes 66 have sufficient distal sharpness and strength, when extended, to penetrate a desired depth into tissue the smooth muscle of the lower esophageal sphincter 18 or the cardia of the stomach 16 (see FIG. 32). The desired depth can range from about 4 mm to about 5 mm.

The electrodes 66 are formed of material that conducts radio frequency energy, e.g., nickel titanium, stainless steel, e.g., 304 stainless steel, or a combination of nickel titanium and stainless steel.

In the illustrated embodiment (see FIG. 4), an electrical insulating material 70 is coated about the proximal end of each electrode 66. When the distal end of the electrode 66 penetrating the smooth muscle of the esophageal sphincter 18 or cardia 20 transmits radio frequency energy, the material 70 insulates the mucosal surface of the esophagus 10 or cardia 20 from direct exposure to the radio frequency energy. Thermal damage to the mucosal surface is thereby avoided. The mucosal surface can also be actively cooled during application of radio frequency energy, to further protect the mucosal surface from thermal damage.

In the illustrated embodiment (see FIG. 4), at least one temperature sensor 80 is associated with each electrode. One temperature sensor 80 senses temperature conditions near the exposed distal end of the electrode 66, a second temperature sensor 80 is located on the corresponding spine 58, which rests against the mucosal surface when the balloon structure 72 is inflated.

The external fluid delivery apparatus 44 is coupled via tubing 12 (see FIG. 1) to connector 48 (see FIG. 4), to supply cooling liquid to the targeted tissue, e.g., through holes in the spines. The external aspirating apparatus 46 is coupled via tubing 14 (see FIG. 1) to connector 50 (see FIG. 4), to convey liquid from the targeted tissue site, e.g., through other holes in the spine or elsewhere on the basket 56. The controller 52 can govern the delivery of processing fluid and, if desired, the removal of aspirated material.

The controller 52 can condition the electrodes 66 to operate in a monopolar mode. In this mode, each electrode 66 serves as a transmitter of energy, and an indifferent patch electrode (described later) serves as a common return for all electrodes 66. Alternatively, the controller 52 can condition the electrodes 66 to operate in a bipolar mode. In this mode, one of the electrodes comprises the transmitter and another electrode comprises the return for the transmitted energy. The bipolar electrode pairs can electrodes 66 on adjacent spines, or electrodes 66 spaced more widely apart on different spines.

Figure 5:
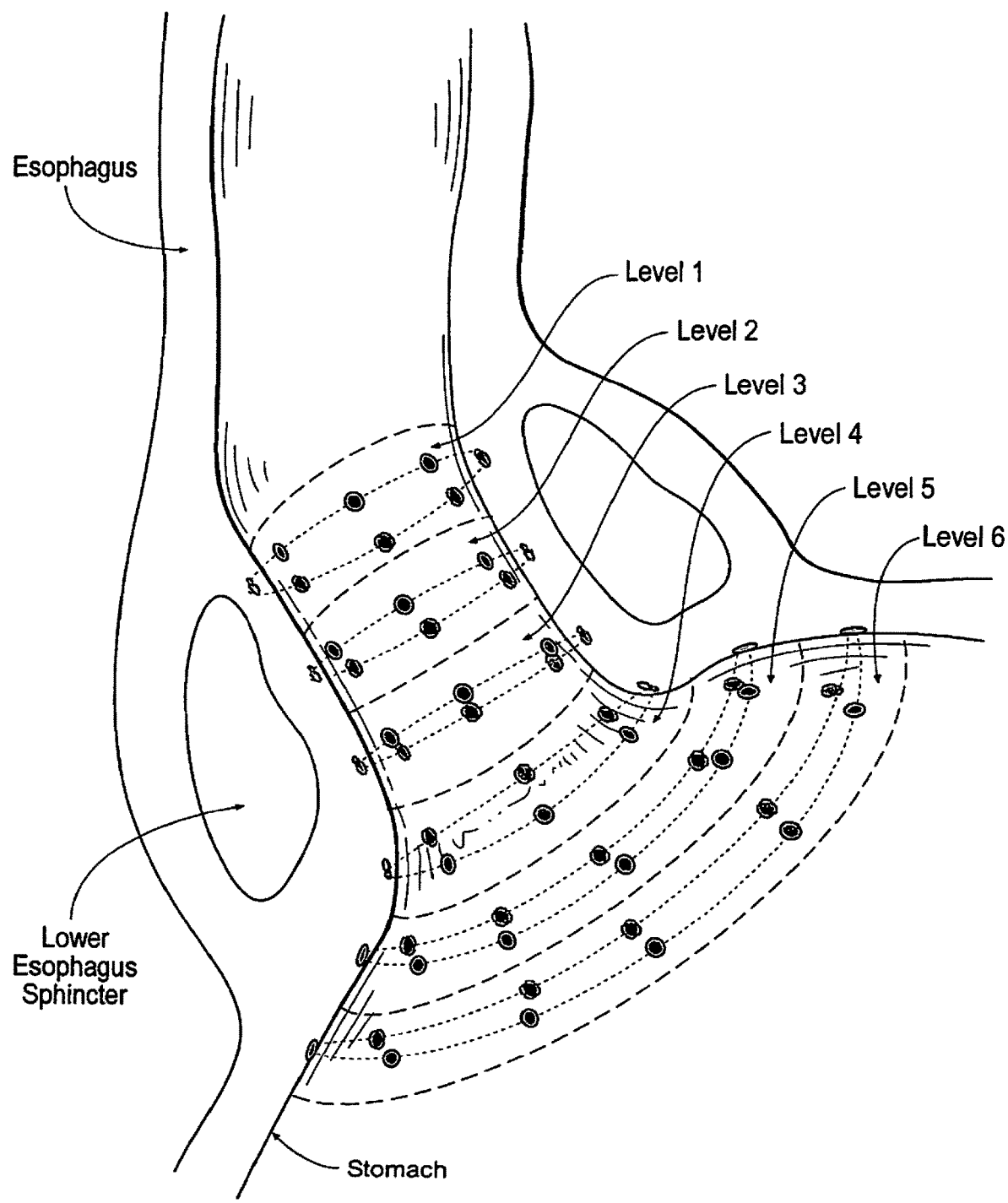
FIG. 5 is a lesion pattern that can be formed by manipulating the device shown FIGS. 2 to 4 in the esophagus at or near the lower esophageal sphincter and in the cardia of the stomach, comprising a plurality of axially spaced lesion levels, each lesion level comprising a plurality of circumferential spaced lesions.

In use, the device 26a is manipulated to create a preferred pattern of multiple lesions comprising circumferential rings of lesions at several axially spaced-apart levels (about 5 mm apart), each level comprising from 8 to 12 lesions. A representative embodiment of the lesion pattern is shown in FIG. 5. As FIG. 5 shows, the rings are preferably formed in the esophagus in regions above the stomach, at or near the lower esophageal sphincter, and/or in the cardia of the stomach. The rings in the cardia are concentrically spaced about the opening funnel of the cardia. At or near the lower esophageal sphincter, the rings are axially spaced along the esophagus.

Multiple lesion patterns can be created by successive extension and retraction of the electrodes 66, accompanied by rotation and/or axial movement of the catheter tube to reposition the basket 56. The physician can create a given ring pattern by expanding the balloon structure 72 and extending the electrodes 66 at the targeted treatment site, to form a first set of four lesions. The physician can then withdraw the electrodes 66, collapse the balloon structure 72, and rotate the catheter tube 30 by a desired amount, e.g., 30-degrees or 45-degrees, depending upon the number of total lesions desired within 360-degrees. The physician can then again expand the structure 72 and again extend the electrodes 66, to achieve a second set of four lesions. The physician repeats this sequence until a desired number of lesions within the 360-degree extent of the ring is formed. Additional lesions can be created at different levels by advancing the operative element axially, gauging the ring separation by external markings on the catheter tube.

As shown in FIG. 5, a desirable pattern comprises an axially spaced pattern of six circumferential lesions numbered Level 1 to Level 6 in an inferior direction, with some layers in the cardia of the stomach, and others in the esophagus above the stomach at or near the lower esophageal sphincter. In the embodiment shown in instant FIG. 5, in the Levels 1, 2, 3, and 4, there are eight lesions circumferentially spaced 45-degrees apart (i.e., a first application of energy, followed by a 45-degree rotation of the basket 56, followed by a second application of energy). In the Levels 5 and 6, there are twelve lesions circumferentially spaced 30-degrees apart (i.e., a first application of energy, followed by a 30-degree rotation of the basket 56, followed by a second application of energy, followed by a 30-degree rotation of the basket 56, followed by a third application of energy). In Level 5, the balloon structure 72 is only partially expanded, whereas in Level 6, the balloon structure 72 is more fully expanded, to provide lesion patterns that increase in circumference according to the funnel-shaped space available in the funnel of the cardia.

B. For Treatment of Lower Gastro-Intestinal Tract

Figure 6:
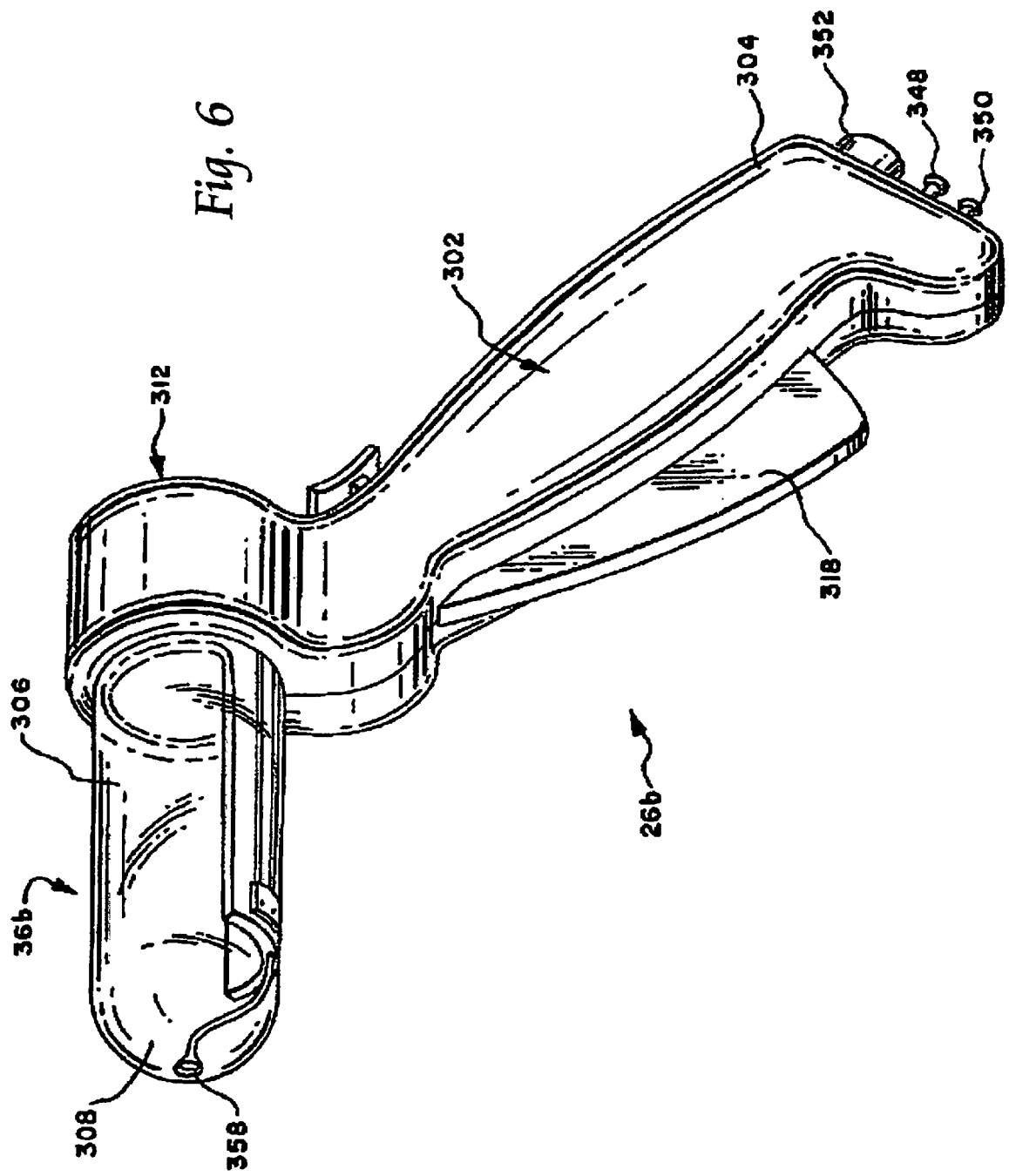
FIG. 6 is a perspective view of another type of treatment device usable in association with the system shown in FIG. 1 to treat tissue in the lower gastrointestinal tract, the treatment device having an array of electrodes shown in a retracted position.
Figure 7:
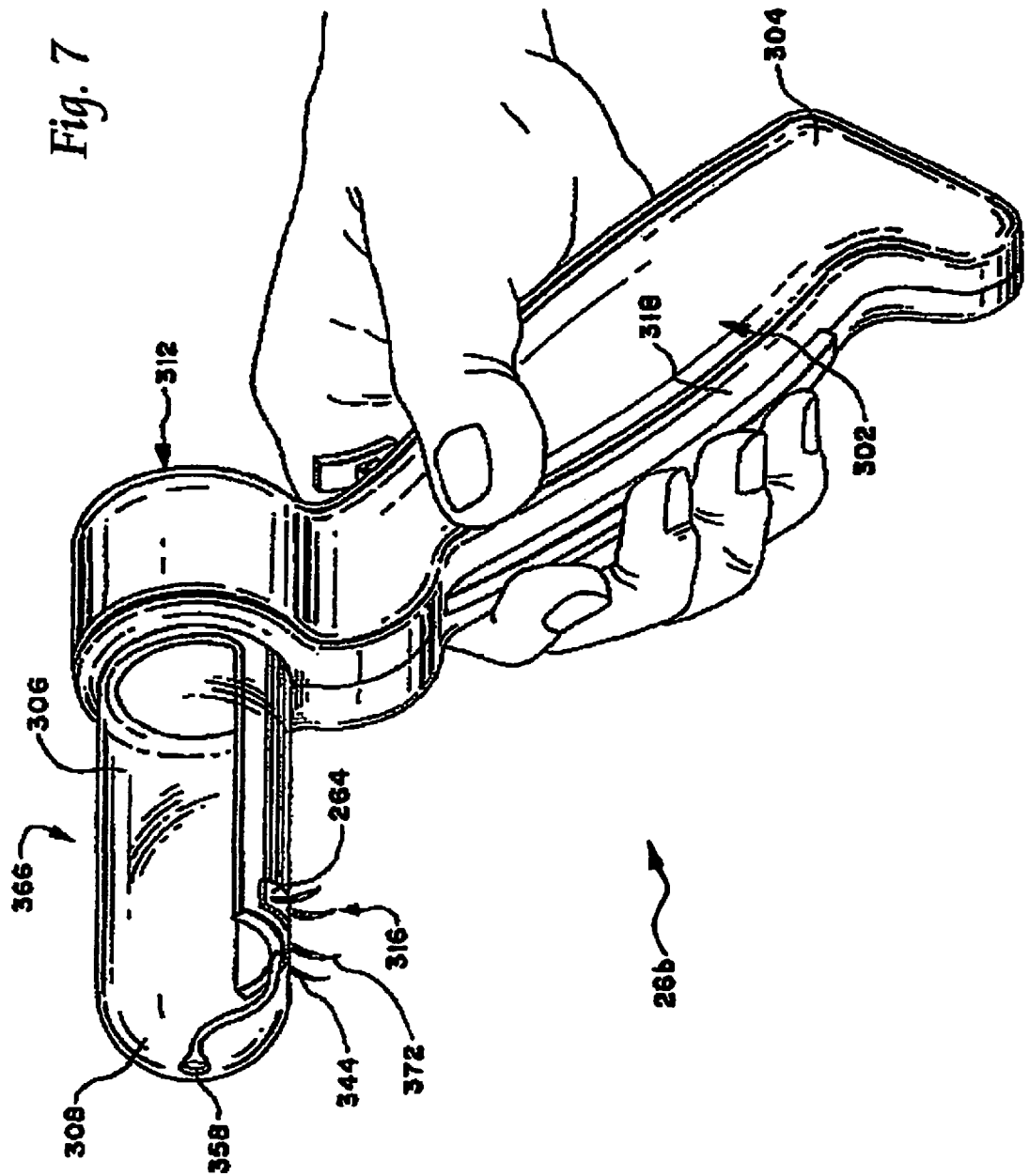
FIG. 7 is a perspective view of the device shown in FIG. 6, with the array of electrodes shown in their extended position.

FIGS. 6 and 7 show a representative embodiment for device 26b, which takes the form of a hand manipulated device 302 for treating sphincter regions in the lower gastro-intestinal tract, and more particularly, the internal and/or external sphincter muscles in the anal canal to treat fecal incontinence. The device 302 includes a hand grip 304 that carries the operative element 36b.

In the illustrated embodiment, the operative element 36b takes the form of a hollow, tubular barrel 306 made from a transparent, molded plastic material. The barrel 306 terminates with a blunt, rounded distal end 308 to aid passage of the barrel 306 through the anal canal, without need for a separate introducer. The hand grip 304 includes a viewing port 312 for looking into the transparent, hollow interior of the barrel 306, to visualize surrounding tissue.

An array of needle electrodes 316 are movably contained in a side-by-side relationship along an arcuate segment of the barrel 306. In the illustrated embodiment, the needle electrodes 316 occupy an arc of about 67.5 degrees on the barrel 306. The needle electrodes 316 are mechanically linked to a finger-operated pull lever 318 on the hand grip 304. By operation of the pull lever 318, the distal ends of the needle electrodes 316 are moved between a retracted position (FIG. 5) and an extended position (FIG. 6 of the '523 patent). An electrical insulating material 344 is coated about the needle electrodes 316 (see FIG. 6 of the '523 patent), except for a prescribed region of the distal ends, where radio frequency energy is applied to tissue. The generator 38 is coupled via the cable 10 to a connector 352, to convey radio frequency energy to the electrodes 316.

Figure 8:
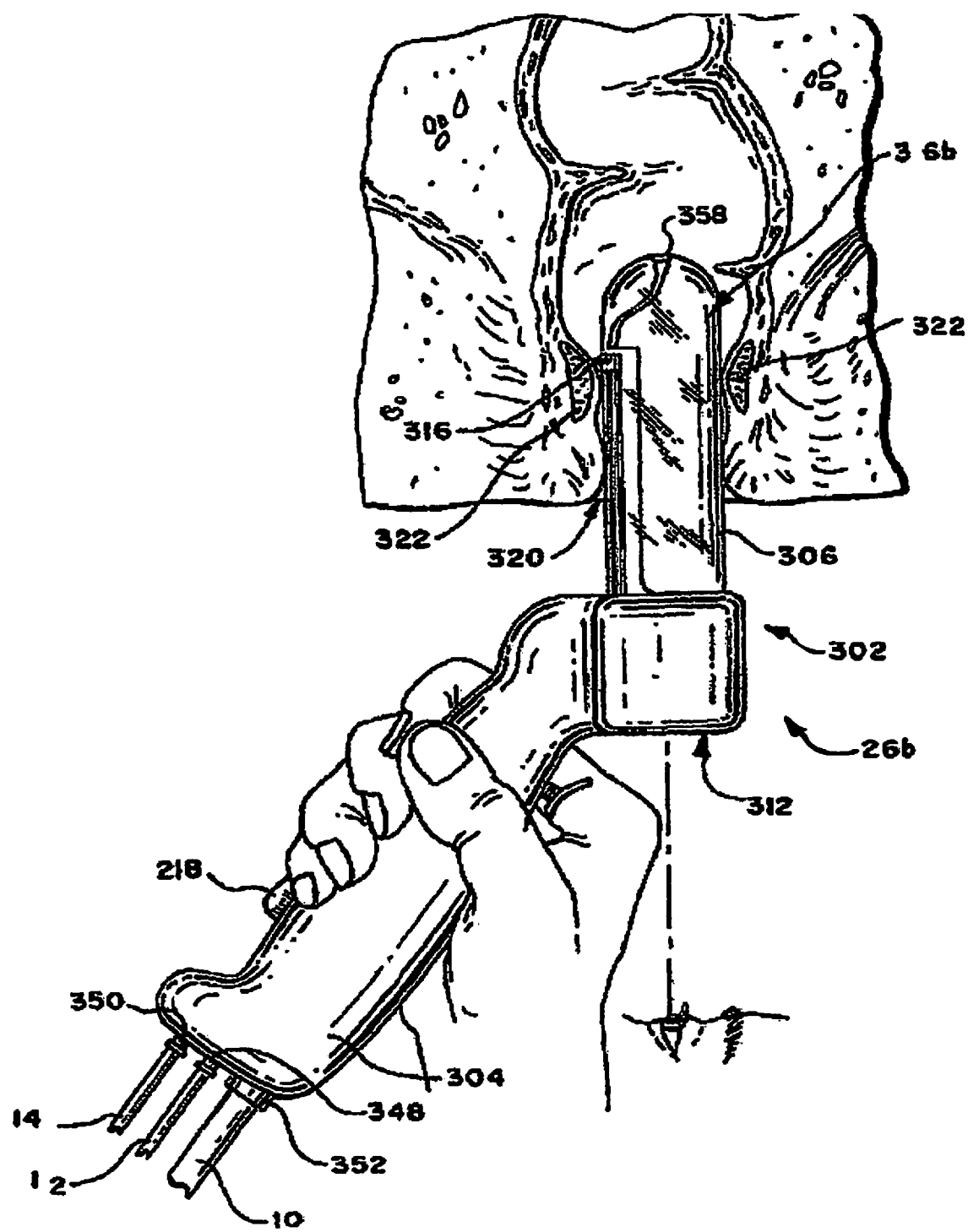
FIG. 8 is a perspective view of the device shown in FIGS. 6 and 7, with the array of electrodes shown in their extended position deployed in the lower gastrointestinal tract to treat sphincter dysfunction in the anal canal.

In use (see FIG. 8), the physician grasps the hand grip 304 and guides the barrel 306 into the anal canal 320. The pull lever 318 is in the neutral position and not depressed, so the needle electrodes 316 occupy their normal retracted position. Looking through the viewing port 312, the physician visualizes the pectinate (dentate) line through the barrel 306. Looking through the barrel 306, the physician positions the distal ends of the needle electrodes 316 at a desired location relative to the pectinate (dentate) line. A fiberoptic can also be located in the barrel 306 to provide local illumination. Once the distal end of the barrel 306 is located at the targeted site, the physician depresses the pull lever 318 (as FIG. 8 shows). The needle electrodes 316 advance to their extended positions. The distal ends of the electrodes 316 pierce and pass through the mucosal tissue into the muscle tissue of the target sphincter muscle. In FIG. 8, the distal end of the electrodes 316 are shown penetrating the involuntary, internal sphincter muscle 322. The physician commands the controller 52 to apply radio frequency energy through the needle electrodes 316. The energy can be applied simultaneously by all electrodes 316, or in any desired sequence.

The external fluid delivery apparatus 44 is coupled via tubing 12 to a connector 348 to convey a cooling liquid, e.g., through holes in the barrel 306, to contact tissue at a localized position surrounding the electrodes 316. The external aspirating apparatus 46 is coupled via tubing 14 to a connector 350 to convey liquid from the targeted tissue site, e.g., through an aspiration port 358 in the distal end 308 of the barrel 306 (see FIGS. 6 and 7).

The barrel 306 (see FIG. 7) also preferably carries temperature sensor 364, one of which is associated with each needle electrode 316. The sensors 364 sense tissue temperature conditions in the region adjacent to each needle electrode 316. Preferably, the distal end of each needle electrode 316 also carries a temperature sensor 372 (see FIG. 7).

In use (see FIG. 9), a preferred pattern of multiple lesions is formed comprises several circumferential rings of lesions in axially spaced-apart levels (about 5 mm apart), each ring comprising 16 lesions in four quadrants of 4 each. The rings are formed axially along the anal canal, at or near the dentate line.

The fluid delivery apparatus 68 conveys cooling fluid for discharge at the treatment site, to cool the mucosal surface while energy is being applied by the needle electrodes 316. The aspirating apparatus 76 draws aspirated material and the processing fluid through the tubing 78 for discharge.

Figure 9:
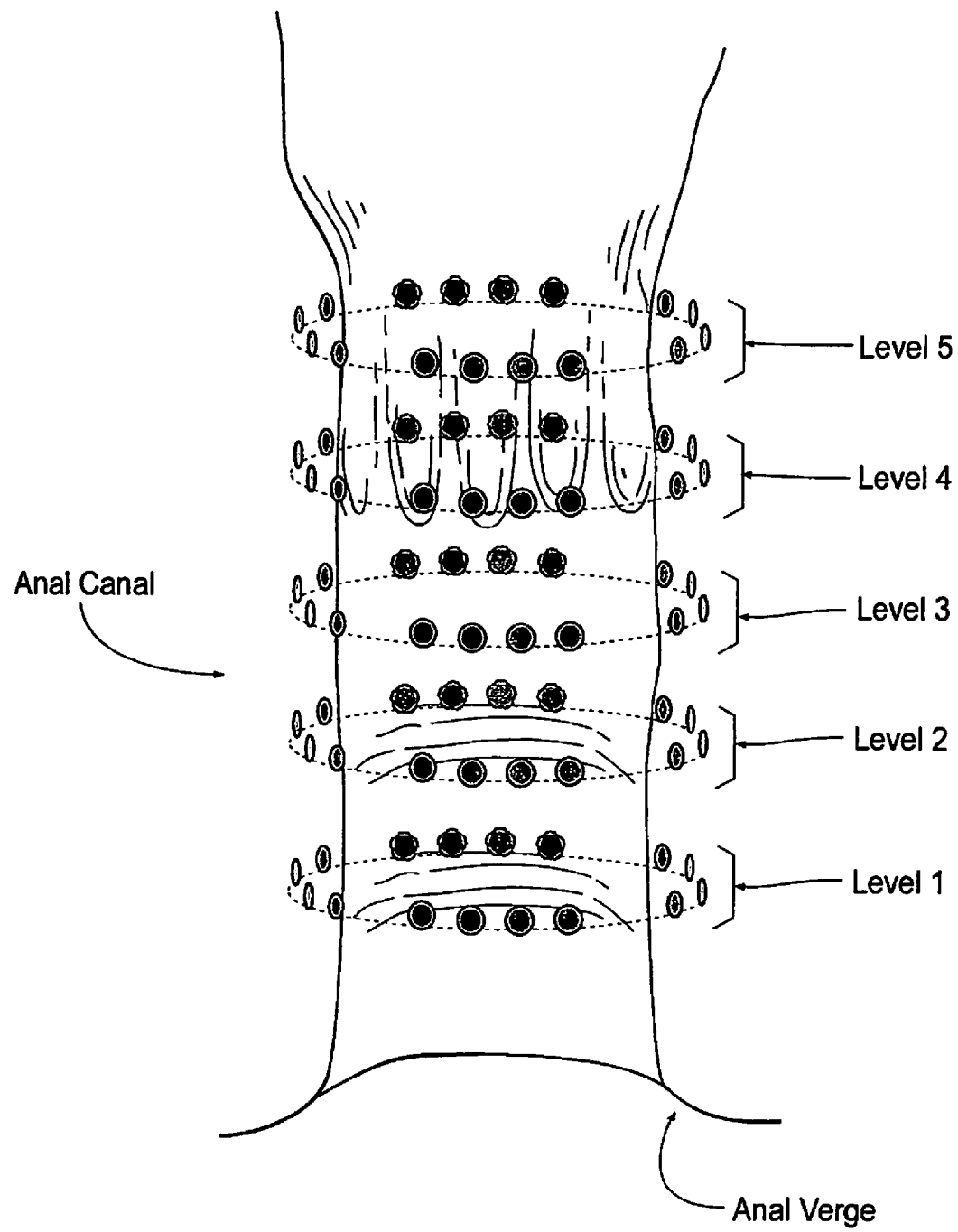
FIG. 9 is a lesion pattern that can be formed by manipulating the device as shown FIG. 8 in the anal canal at or near the anal sphincter, comprising a plurality of axially spaced lesion levels, each lesion level comprising a plurality of circumferential spaced lesions.

Referring to FIG. 9, the array of needle electrodes 316 is positioned at Level 1 to create four multiple lesions in the first quadrant. Upon the satisfactory creation of the lesion pattern in the first quadrant of Level 1, as just described, the physician actuates the button 64 to release the locking pawl 58 from the detent 62. The pull lever 52 returns to the spring-biased neutral position, thereby moving the needle electrodes 316 back to their retracted positions. Still grasping the hand grip 40 and visualizing through the viewing port 46, the physician moves the barrel 5 mm axially upward to Level 2, the first quadrant. The physician again deploys the needle electrodes 48 and performs another lesion generating sequence. The physician repeats this sequence of steps until additional number of lesion patterns are formed within the axially spaced first quadrants in Levels 1, 2, 3, 4, and 5.

Still grasping the hand grip 40 and visualizing through the viewing port 46, the physician returns to level 1, and rotates the barrel 42 a selected arcuate distance at the level of the first lesion pattern 94 to the second quadrant, i.e., by rotating the barrel 42 by ninety degrees.

The physician again deploys the needle electrodes 48 and performs another lesion generating sequence at quadrant 2 of Level 1. The physician then moves the barrel axially upward in 5 mm increments, at a number of axially spaced levels 2, 3, 4, and 5 generally aligned with lesion patterns 96, 98, and 100. Lesions are formed in this way in the second quadrant of Levels 1, 2, 3, 4, and 5.

The physician repeats the above described sequence two additional times, returning the barrel to level 1 and rotating the barrel 42 at successive intervals and axially repositioning the barrel 42 to form the lesion patterns quadrants 3 and 4 in the Levels 1, 2, 3, 4, and 5. This protocol forms a composite lesion pattern 102, which provides a density of lesions in the targeted sphincter tissue region to provoke a desired contraction of the sphincter tissue.

III. System Operation

In the illustrated embodiment (see FIGS. 10A and 10B), the radio frequency generator 38, the controller 52 with I/O device 54, and the fluid delivery apparatus 44 (e.g., for the delivery of cooling liquid) are integrated within a single housing 400.

Figure 10A:
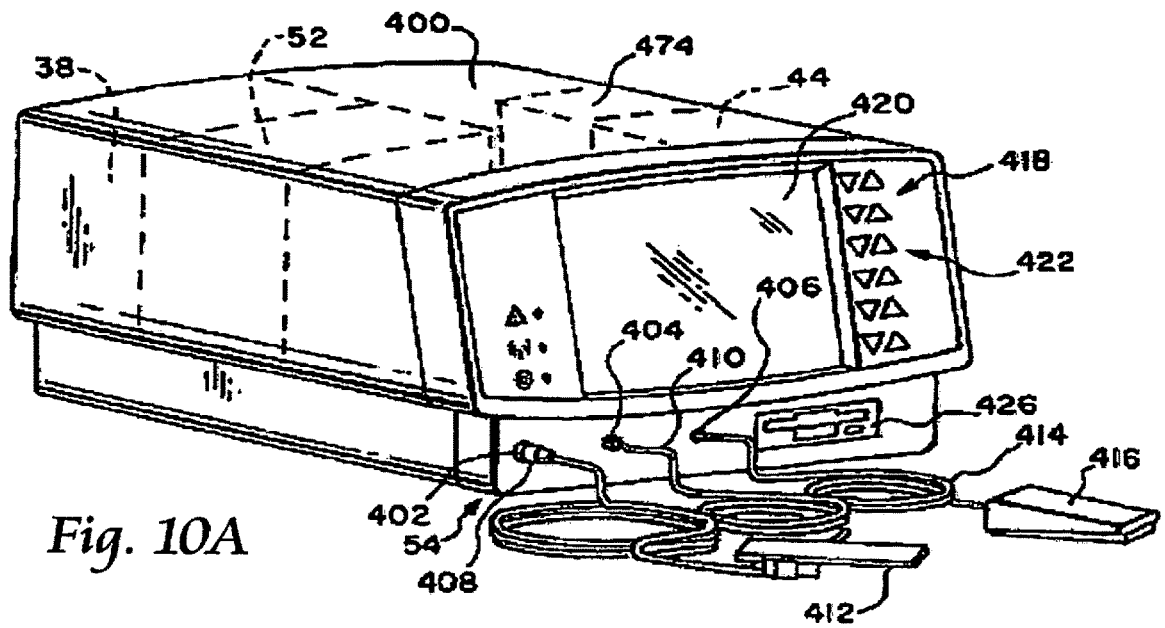
FIGS. 10A and 10B are, respectively, left and right perspective views of one embodiment of an integrated device incorporating features of the system shown in FIG. 1 and usable with either treatment device shown in FIG. 2 or 6 for treating body sphincters and adjoining tissue regions, and also having controller that a graphical user display for visually prompting a user in a step-wise fashion to use a treatment device to perform a process of forming a pattern of lesions in a body region like that shown in FIG. 5 or 9, to guide the user so that individual lesions desired within a given level are all formed, and that a given level of lesions is not skipped.
Figure 10B:
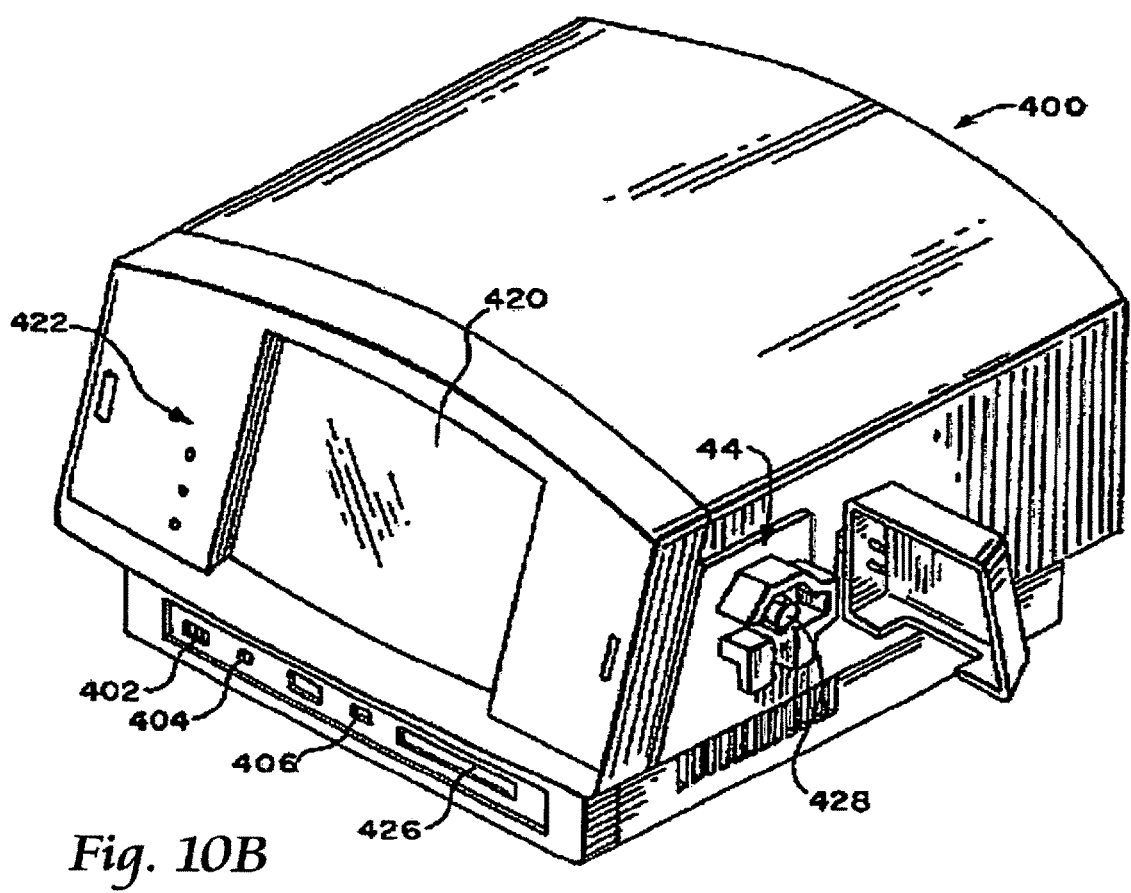

The I/O device 54 couples the controller 52 to a display microprocessor 474 (see FIG. 10A). The display microprocessor 474 is coupled to a graphics display monitor 420 in the housing 400. The controller 52 implements through the display microprocessor 474 the graphical user interface, or GUI, which is displayed on the display monitor 420. The graphical user interface is can be realized with conventional graphics software using the MS WINDOWS® application. The GUI 424 is implemented by showing on the monitor 420 basic screen displays.

A. Set-Up

Figure 11:
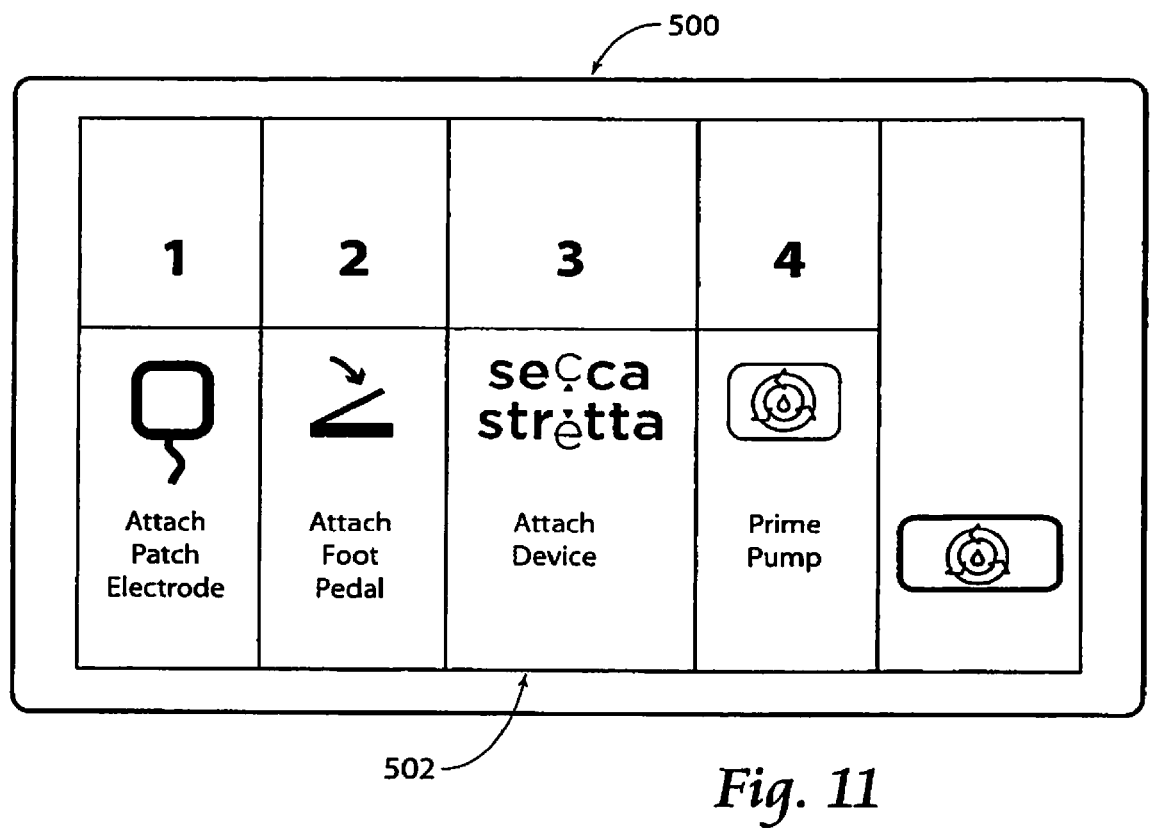
FIG. 11 is a representative graphical user set-up display generated by the controller prompting the user with numbers and/or text and/or icons through the set-up and connection steps prior to a treatment procedure.

Upon boot-up of the CPU (see FIG. 11), the operating system implements the SET-UP function for the GUI 500. The GUI displays an appropriate start-up logo and title image (not shown), while the controller 52 performs a self-test. An array of SETUP prompts 502 leads the operator in a step-wise fashion through the tasks required to enable use of the generator and device. The physician can couple the source of cooling liquid to the appropriate port on the handle of the device 26a/26b (see FIG. 10A, as previously described) and load the tubing leading from the source of cooling liquid (e.g., a bag containing sterile water) into the pump rotor 428 (see FIG. 10B). The physician can also couple the aspiration source 46 to the appropriate port on the handle of the treatment device 26a/26b (as also already described). The physician can also couple the patch electrode 412 and foot pedal 416 (shown in FIG. 10A). In the SET-UP prompt array 502, a graphic field of the GUI 500 displays one or more icons and/or alpha-numeric indicia 502 that prompt the operator to connect the return patch electrode 412, connect the foot pedal or switch 416, connect the selected treatment device 26a (designed by its trademark STRETTA®) or 26b (designated by its trademark SECCA®), and to prime the irrigation pump 44.

The controller 52 ascertains which device 26a or 26b has been selected for use by reading a coded identification component residing in the handle of the device 26a or 26b. Based upon this input, the controller 52 proceeds to execute the preprogrammed control and graphical GUI command functions for the particular device 26a and 26b that is coupled to the generator.

Figure 12:
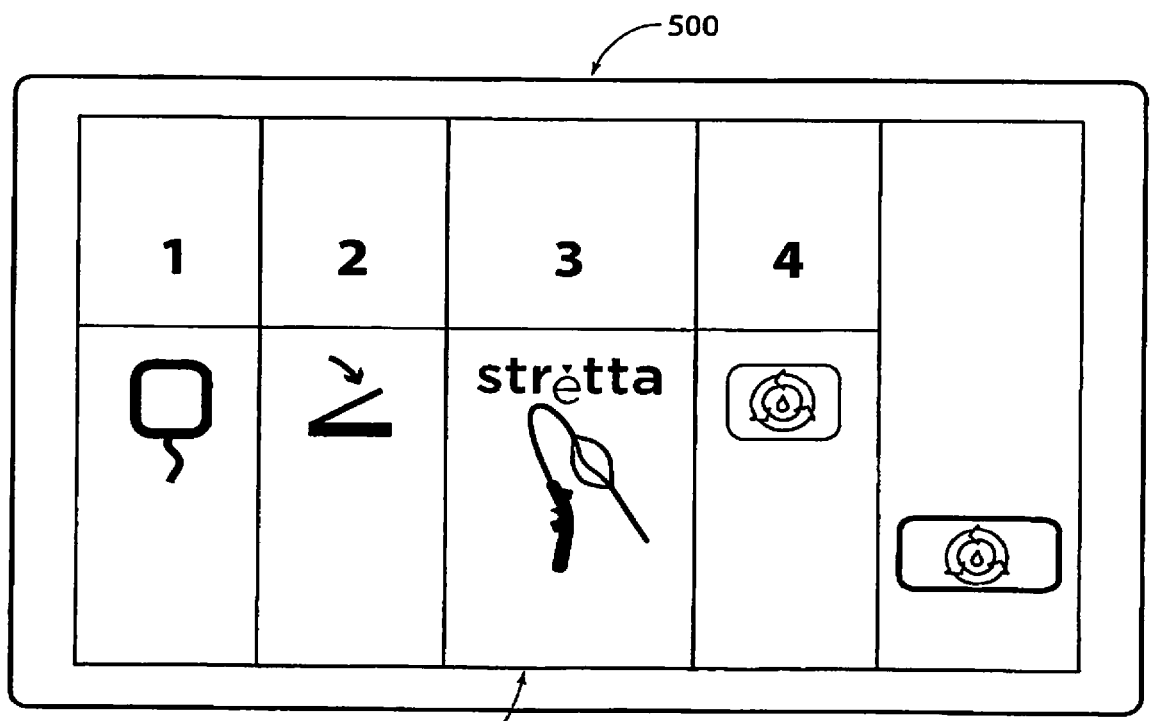
FIG. 12 is a representative graphical user set-up display generated by the controller upon identifying the connection of a device like that shown in FIGS. 2 to 4 (identified by the trademark STETTA®).
Figure 13:
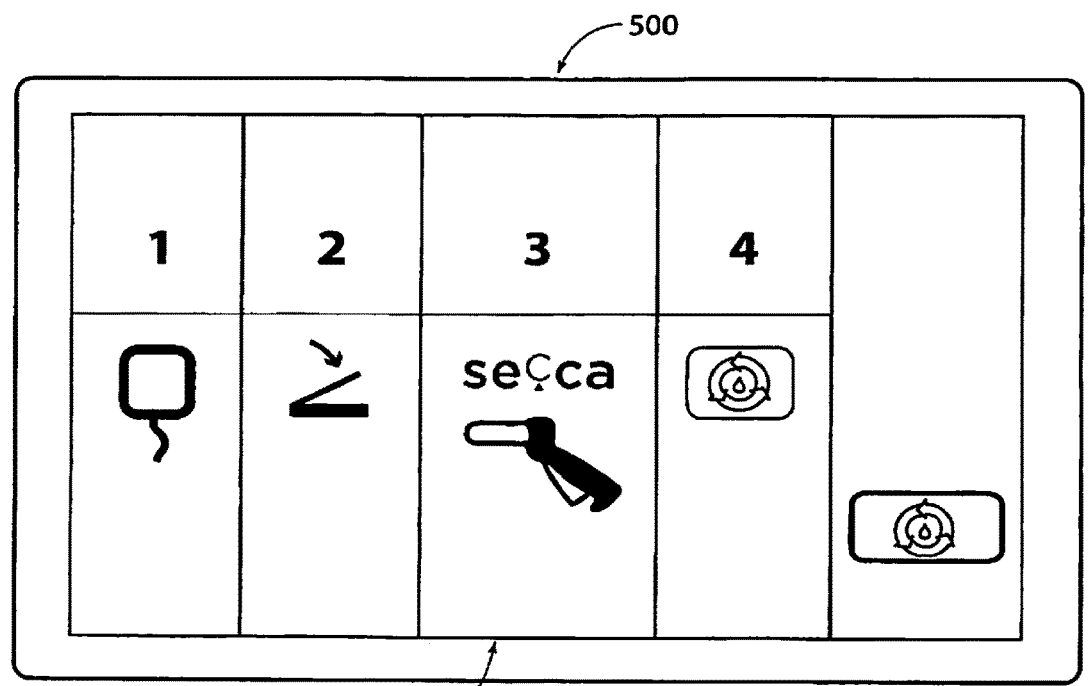
FIG. 13 is a representative graphical user set-up display generated by the controller upon identifying the connection of a device like that shown in FIGS. 6 to 8 (identified by the trademark SECCA®).

If the identification code for the device 26a, (STRETTA®) is registered, the GUI displays an appropriate start-up logo and title image for the device 26a (see FIG. 12). Likewise, if the identification code for the device 26b (SECCA®) is registered, the GUI displays an appropriate start-up logo and title image for the device 26b (FIG. 13).

B. Treatment Screens (UGUI and LGUI)

Upon completion of the SET-UP operation, the controller 52 proceeds to condition the generator and ancillary equipment to proceed step-wise through a sequence of operational modes. The operational modes have been preprogrammed to achieve the treatment protocol and objective of the selected device 26a/26b. The conduct of these operational modes and the appearance of the graphical user interface that guides and informs the user during the course of the selected procedure can differ between devices 26a and 26b.

Figure 14A:
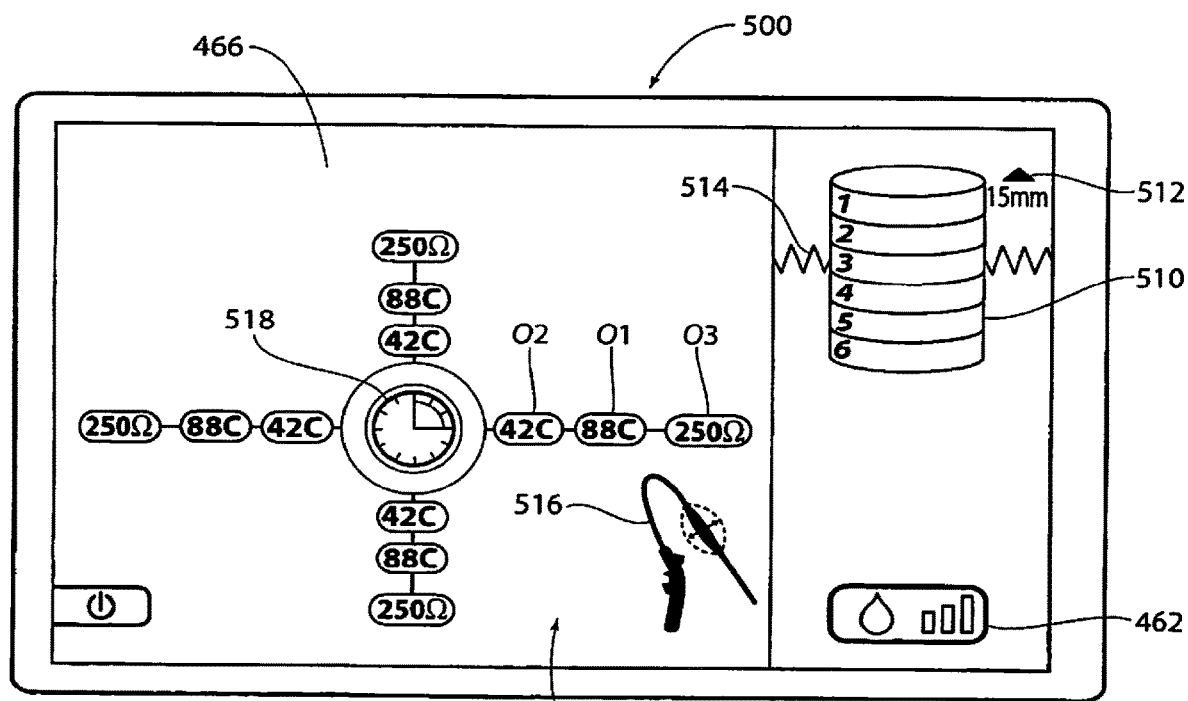
FIGS. 14-A to 14-O are representative graphical user treatment displays generated by the controller for visually prompting a user to use a treatment device like that shown in FIGS. 2 to 4 in a step-wise fashion to perform a process of forming a pattern of lesions in an esophagus like that shown in FIG. 5, the graphical user display guiding the user and creating a visual record of the progress of the process from start to finish, so that individual lesions desired within a given level are all formed, and that a given level of lesions is not skipped.
Figure 15A:
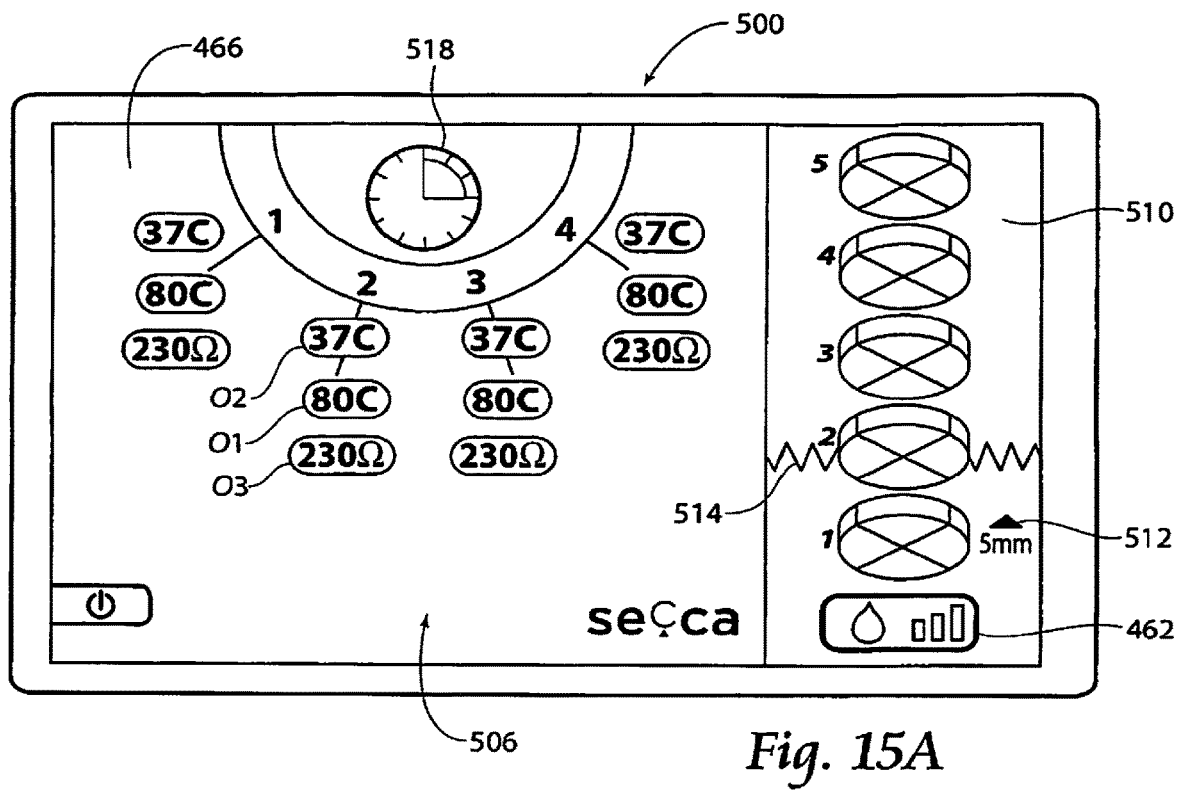
FIGS. 15A to 15I are representative graphical user treatment displays generated by the controller for visually prompting a user to use a treatment device like that shown in FIGS. 6 to 8 in a step-wise fashion to perform a process of forming a pattern of lesions in an anal canal like that shown in FIG. 9, the graphical user display guiding the user and creating a visual record of the progress of the process from start to finish, so that individual lesions desired within a given level are all formed, and that a given level of lesions is not skipped.

For ease of description, the GUI 500 displays for the upper gastro-intestinal procedure (i.e., for the device 26a) a treatment screen that will in shorthand be generally called UGUI 504 (FIG. 14A). Likewise, the GUI displays for the lower gastro-intestinal procedure (i.e., for the device 26b) a treatment screen that will in shorthand be generally called LGUI 506 (FIG. 15A).

In both the UGUI 504 (FIG. 14A) and LGUI 506 (FIG. 15A), there is a parameter icon 462 designating cooling fluid flow rate/priming. In both the UGUI 504 and the LGUI 506, the Flow Rate/Priming Icon 462 shows the selected pump speed by the number of bars, one bar highlighting a low speed, two bars highlighting a medium speed, and three bars highlighting a high speed.

Each UGUI 504 (FIG. 14A) and LGUI 506 (15A) includes an Electrode Icon 466. In general, each Electrode Icon 466 comprises an idealized graphical image, which spatially models the particular multiple electrode geometry of the treatment device 26a/26b that has been coupled to the controller 42. Just as the multiple electrode geometries of the devices 26a and 26b differ, so, too, does the Electrode Icon 466 of the UGUI 504 differ from the Electrode Icon 466 of the LGUI 506.

As FIG. 14A shows, in the UGUI 504, four electrodes are shown in the graphic image of the Icon 466, which are spaced apart by 90 degrees. This graphic image reflects the geometry of the four-electrode configuration of the device 26a, as shown in FIG. 4.

As FIG. 15A shows, in the LGUI 506, four electrodes are shown in the graphic image of Icon 466 in a circumferentially spaced relationship along a partial arcuate sector. This graphic image reflects the arrangement of electrodes on the treatment device 26b, as shown in FIG. 7.

For each electrode, the respective Icon 466 incorporates graphic regions O1, O2, and O3 in the spatial display. Regions O1 and O2 display temperature conditions encountered for that electrode. Region O1 numerically displays the magnitude of sensed electrode tip temperature in UGUI 504 (FIG. 14A) and LGUI 506 (FIG. 15A). Region O2 numerically displays sensed tissue temperatures for that electrode in UGUI 504 (FIG. 14A) and LGUI 506 (FIG. 15A). Region O3 displays the derived impedance value for each electrode. Both UGUI 504 and LGUI 506 display instantaneous, sensed temperature readings from the tip electrode and tissue surface, as well as impedance values, which are continuously displayed in spatial relation to the electrodes in the regions O1, O2, and O3.

The numeric displays of the regions O1/O2/O3 can be blanked out for a given electrode if the corresponding electrode/channel has been disabled, either by the physician or by a sensed out-of-bounds condition. An "acceptable" color indicator (e.g., green) can also displayed in the background of the regions O1/O2/O3 as long as the sensed condition is within the desired pre-established ranges. However, if the sensed conditions fall outside the desired range, the color indicator changes to an "undesirable" color indicator (e.g., to grey), and numeric display is blanked out.

There is also a Lesion Level Icon 510 in each display UGUI 504 and LGUI 506, adjacent to the respective Electrode Icon 466. The Lesion Level Icon 510 comprises an idealized graphical image, which spatially models the desired lesion levels and the number of lesions in each level. Just as the lesion patterns created by the devices 26a and 26b differ, so, too, does the Lesion Level Icon 510 of the UGUI 504 differ from the Electrode Icon 466 of the LGUI 506.

As will be described in greater detail later, the Lesion Level Icons 510 change in real time, to step-wise guide the physician through the procedure and to record the progress of the procedure from start to finish. In many fundamental respects, the look and feel of the Lesion Level Icons 510 for the LGUI 504 and the LGUI 506 are similar, but they do differ in implantation details, due to the difference of the protocols of lesion formation.

Exemplary changes in the Lesion Level Icons 510 for the UGUI 504 and the LGUI 506 will now be described.

1. The UGUI

In the UGUI 504 (see FIG. 14A), six numbered Lesion Levels 1, 2, 3, 4, 5, and 6 are displayed, to correspond with the lesion levels already described and shown in FIG. 5. The UGUI 504 also displays a squiggle line 514, which marks where the physician has visualized a selected anatomic home base reference for the formation of lesions within the esophagus for treatment. Guided by the UGUI 504, lesions are placed relative to this anatomic home base.

In preparation for the treatment, the physician visualizes in the esophagus the Z-line or other desired anatomic landmark. Markers are arranged at 5 mm intervals along the catheter tube. Upon visualizing the Z-line, the physician notes the external marker on the catheter tube that corresponds to this position. With reference to the markers, the physician can then axially advance or retract the catheter tube in 5 mm increments, which correspond to the desired spacing between the lesion levels. This orientation of lesion levels is also shown in FIG. 5.

The UGUI 504 graphically orients the location of Lesion Levels 4, 5, and 6 relative to this anatomical base, displaying Lesion Levels either below (inferior to) the squiggle line 514 (Lesion Levels 4, 5, and 6) or at or above the squiggle line 514 (Lesion Levels 1, 2, and 3).

As will be described, the UGUI 504 graphically changes the display of the the Lesion Levels, depending upon the status of lesion formation within the respective levels.

FIG. 14A shows a representative first graphical form of a given lesion level. The graphical form comprises, e.g., a cylinder that faces edgewise on the UGUI 504, as is shown for Lesion Levels 1 to 6 in FIG. 14A. This graphical form indicates at a glance that no lesions are present in the respective lesion levels.

As is shown in FIG. 14A, next to the graphical form of the edgewise cylinder of Lesion Level 1 is a Guide Marker 512. The Guide Marker 514 indicates that formation of lesions in Lesion Level 1 is the first to be indicated. A numeric value (15 mm) is displayed in association with the edgewise cylinder of Lesion Level 1, which indicates that Lesion Level 1 is 15 mm from the anatomic landmark. The orientation of Lesion Level 1 above (superior to) the squiggle line 514 guides the physical to advance the catheter tube upward from the anatomic marker by 15 mm, to place it at Lesion Level 1. A Balloon Icon 516 prompts the physician to expand the basket of the device 26a at Lesion Level 1.

Figure 14B:
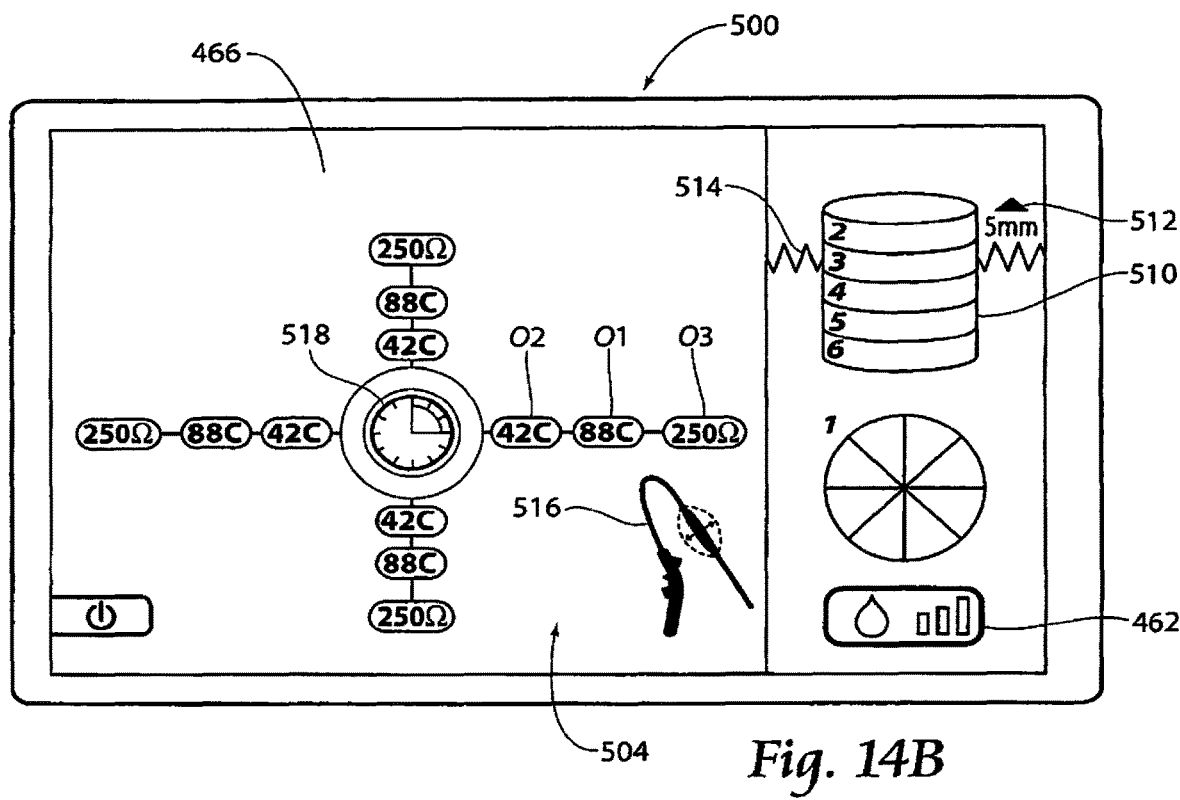

Upon sensing electrode impedance, indicating contact with tissue at Lesion Level 1 (or in response to another input indicating deployment of the device 26a at the desired lesion level), the controller commands the UGUI 504 to change the graphical form of Lesion Level 1 to a second graphical form, which is shown in FIG. 14B. The second graphical form (shown in FIG. 14B) is different than the first graphical form (shown in FIG. 14A). The graphical form comprises, e.g., a segmented circle, with a numeric indicator next to it. This is shown for Lesion Level 1 in FIG. 14B. In visual effect, the second graphical form shows the previously cylinder form rotated for viewing along its axis. The number of segments shown (in FIG. 14B, there are eight segments) corresponds with the number of lesions that are to be formed at Lesion Level 1.

In FIG. 14B, all segments of the circle are unmarked. This graphical form indicates at a glance that (i) formation of lesions at this lesion level is now indicated (due to the axial circle view of the lesion level icon), (ii) eight circumferentially spaced lesions are to be formed (due to the number of segments); (iii) no lesions have as yet been formed (by the lack of other markings in the segments).

The location of the Marker 512 also changes to align with Lesion Level 2, with a numeric indicator of 5 mm. This informs the physician that, after Lesion Level 1, the next lesion level to be treated is Lesion Level 2, which is 5 mm below (inferior to) Lesion Level 1.

With the device 26a positioned at Lesion Level 1, the physician actuates the electrodes for a first pre-set period.

Figure 14C:
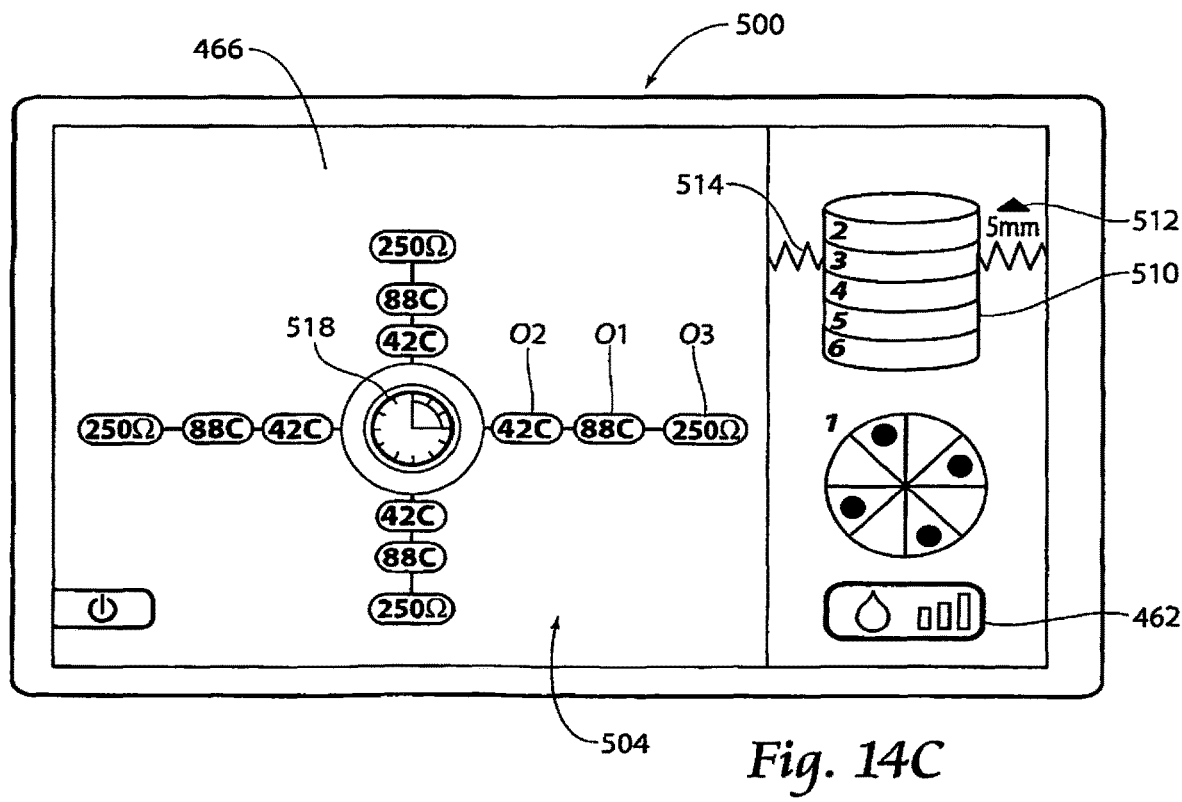

The balloon icon 516 disappears as treatment progresses on a given level. A Timer Icon 518 shows the application of radio frequency energy for the pre-set period. At the end of this pre-set period (see FIG. 14C), treatment indicia (e.g., dots) appear in four segments of the graphical segmented circle, indicating the formation of the first four lesions, as well as their spatial orientation.

Figure 14D:
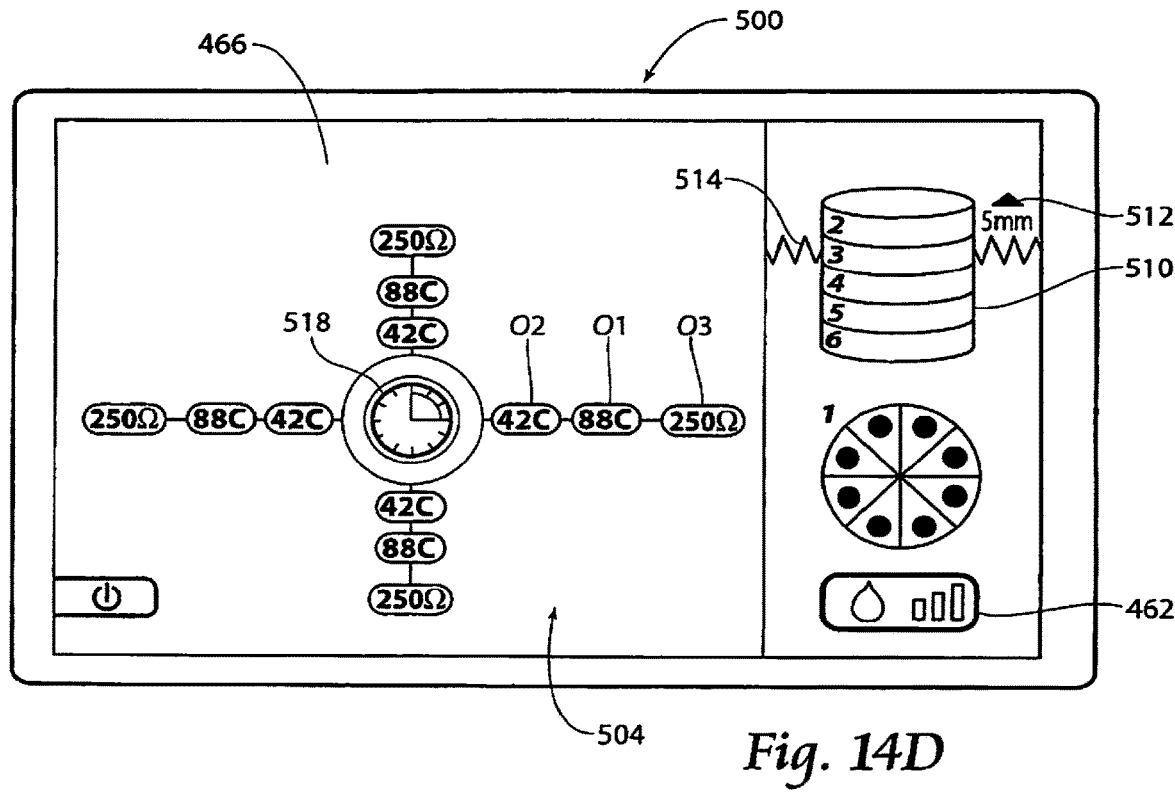

The open segments remaining in the segmented circle prompt the physician to rotate the basket by 45-degrees, and actuate the electrodes for second time. After the pre-set period (tracked by the Timer Icon 518) (see FIG. 14D), more treatment indicia (the dots) appear in the remaining segments of the circle. This indicates that all the lesions prescribed for Lesion Level 1 have been formed, and to deflate the basket and move to the next treatment level. The Marker 512 that is displayed directs the physician to Lesion Level 2, which is 5 mm below Lesion Level 1. The Balloon Icon 516 can reappear to prompt the physician to deflate the balloon.

Figure 14E:
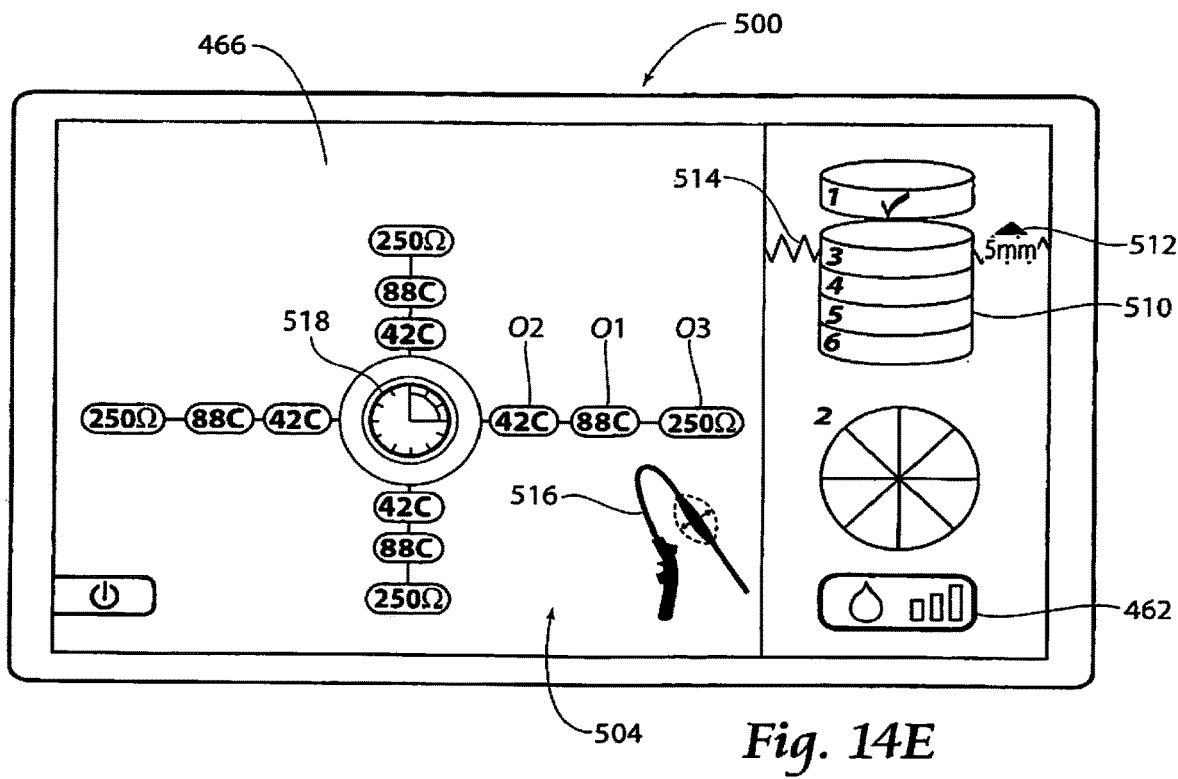

The physician is thereby prompted to deflate the basket, move to Lesion Level 2, and expand the basket. As FIG. 14E shows, upon sensing electrode impedance, indicating contact with tissue at Lesion Level 2, the UGUI 504 changes the graphical form of Lesion Level 1 back to an edgewise cylinder. The edgewise cylinder for Lesion Level 1 includes an indicator, e.g., checkmark, to indicate that Lesion Level 1 has been treated (as shown in FIG. 14E). The insertion of the treatment completed indicator is yet another graphical form the UGUI 504 displays to communicate status information to the physician.

Also referring to FIG. 14E, upon sensing electrode impedance, indicating contact with tissue at Lesion Level 2, the UGUI 504 changes the graphical form of Lesion Level 2 to the second graphical form, comprising, e.g., the segmented circle, as already described. This is shown for Lesion Level 2 in FIG. 14E. The location of the Marker 512 also changes to align with Lesion Level 3, with a numeric indicator of 5 mm. This informs the physician that after Lesion 2, the next lesion level will be Lesion Level 3, which is 5 mm below (inferior to) Lesion Level 2.

Figure 14F:
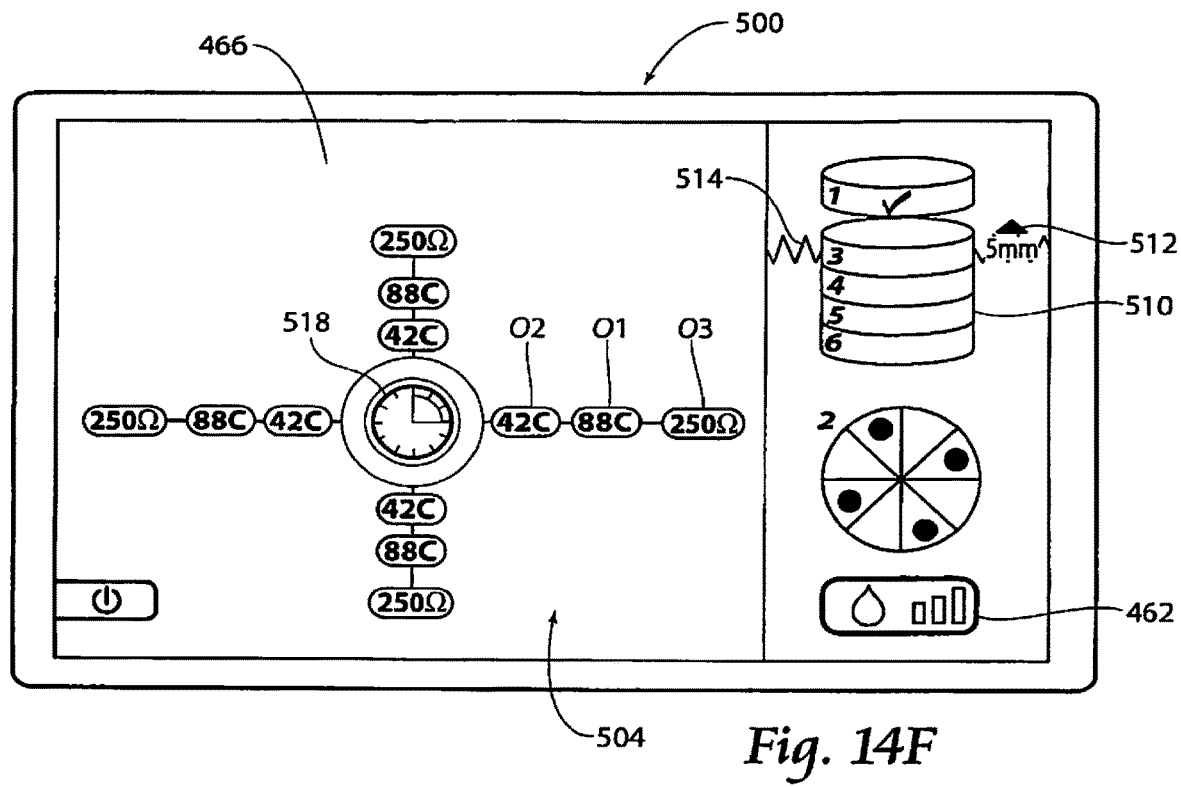
Figure 14G:
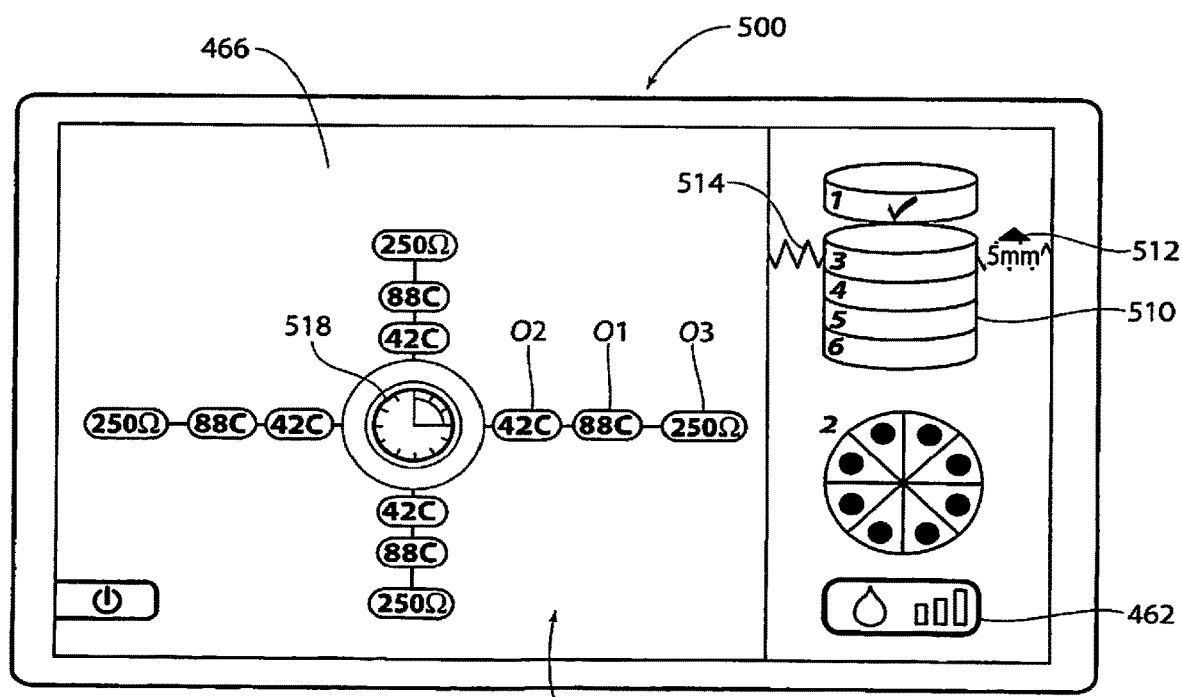

As shown in FIGS. 14F and 14G, with the device 26a positioned at Lesion Level 2, the physician actuates the electrodes for a first pre-set period, then rotate the device 26a 45-degrees, and actuate the electrodes for the second pre-set period. The Timer Icon 518 reflects the application of radio frequency energy for the pre-set periods, and the treatment indicia (e.g., dots) are added to the segments of the graphical segmented circle, indicating the formation of the first four lesions (FIG. 14F) and the next four lesions (FIG. 14G), as well as their spatial orientation.

Upon formation of the eight lesions in Lesion Level 2, the balloon icon 518 again appears. This indicates that all the lesions prescribed for Lesion Level 2 have been formed, and to deflate the basket and move to the next treatment level. The Marker 512 that is displayed directs the physician to Lesion Level 3, which is 5 mm below Lesion Level 2.

Figure 14H:
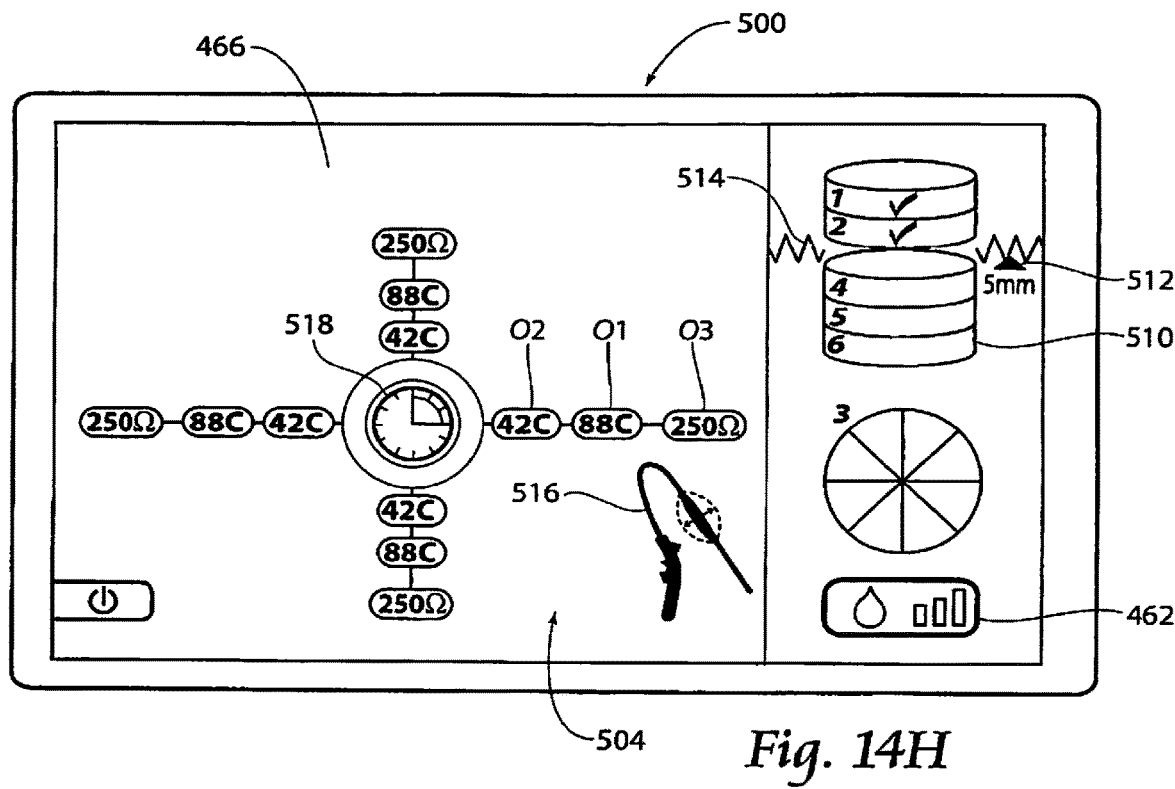

The physician is thereby prompted to deflate the basket, move to Lesion Level 3, and expand the basket. Upon sensing electrode impedance, indicating contact with tissue at Lesion Level 3 (see FIG. 14H), the UGUI 504 changes the graphical form of Lesion Level 2 back to an edgewise cylinder (as FIG. 14H shows). The edgewise cylinder for Lesion Level 2 now includes an indicator, e.g., the checkmark, to indicate that Lesion Level 2 has been treated (as FIG. 14H also shows).

Figure 14I:
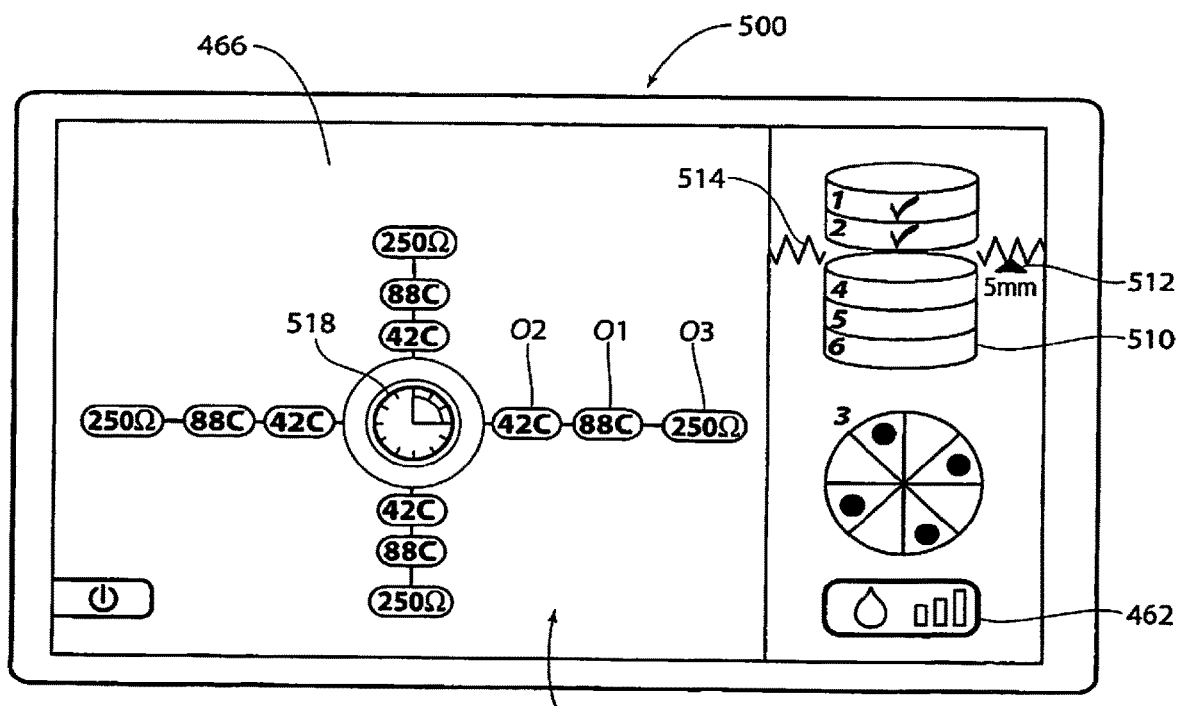

As FIG. 14I also shows, upon sensing electrode impedance, indicating contact with tissue at Lesion Level 3, the UGUI 504 changes the graphical form of Lesion Level 3 to the second graphical form, comprising, e.g., the segmented circle, as already described. This is shown for Lesion Level 3 in FIG. 14H. The location of the Marker 512 also changes to align with Lesion Level 4, with a numeric indicator of 5 mm. This informs the physician that after Lesion 3, the next lesion level will be Lesion Level 3, which is 5 mm below (inferior to) Lesion Level 3.

Figure 14J:
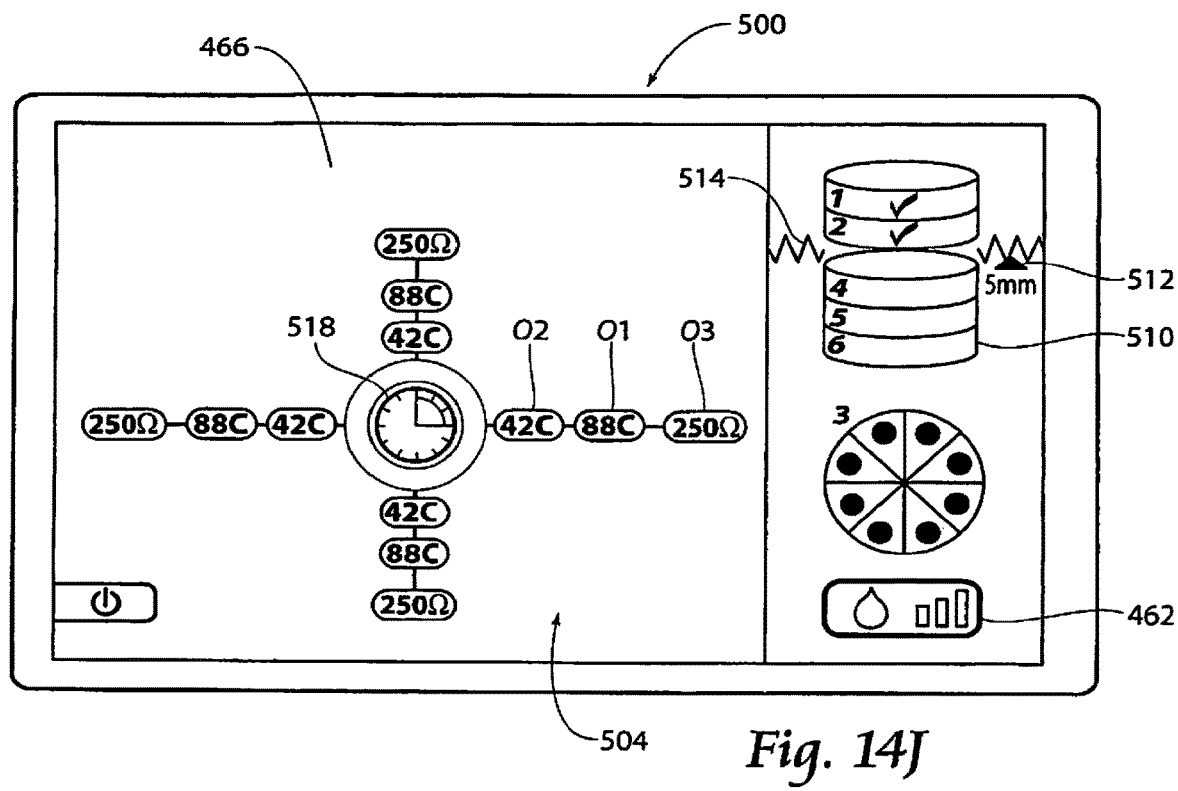
Figure 14K:
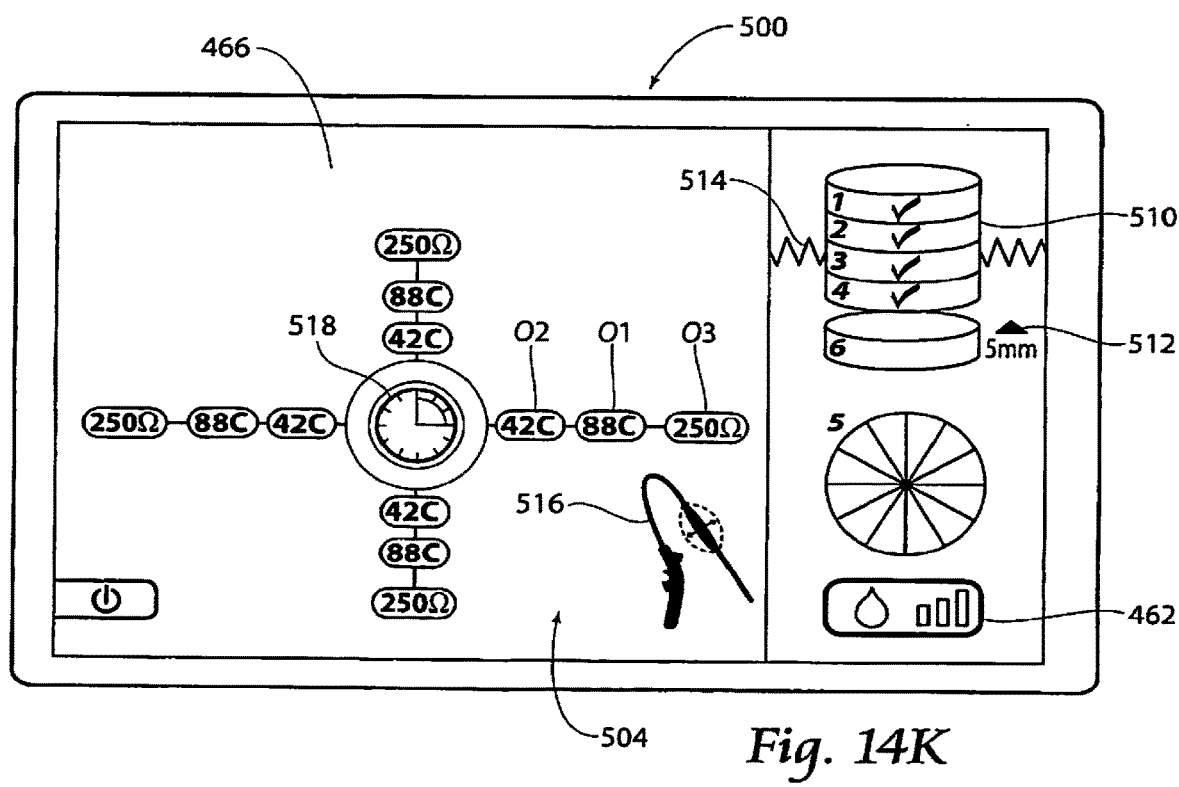
Figure 14L:
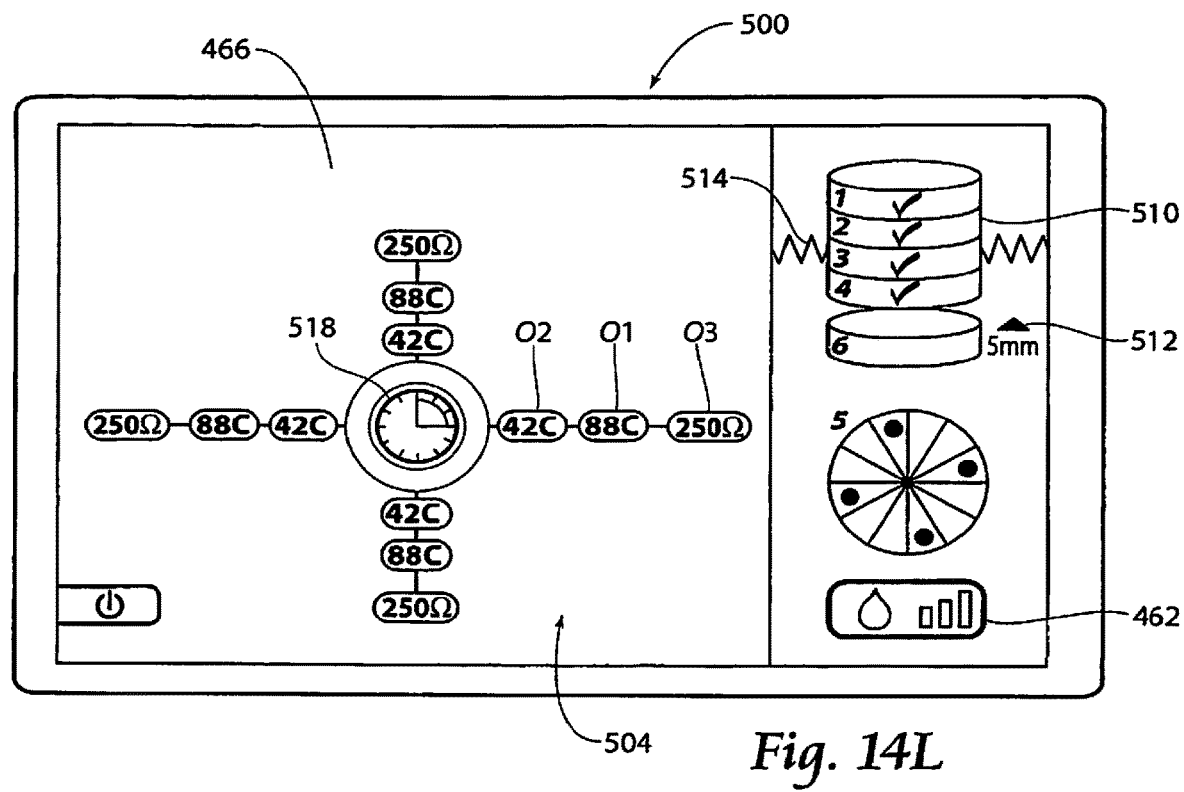
Figure 14M:
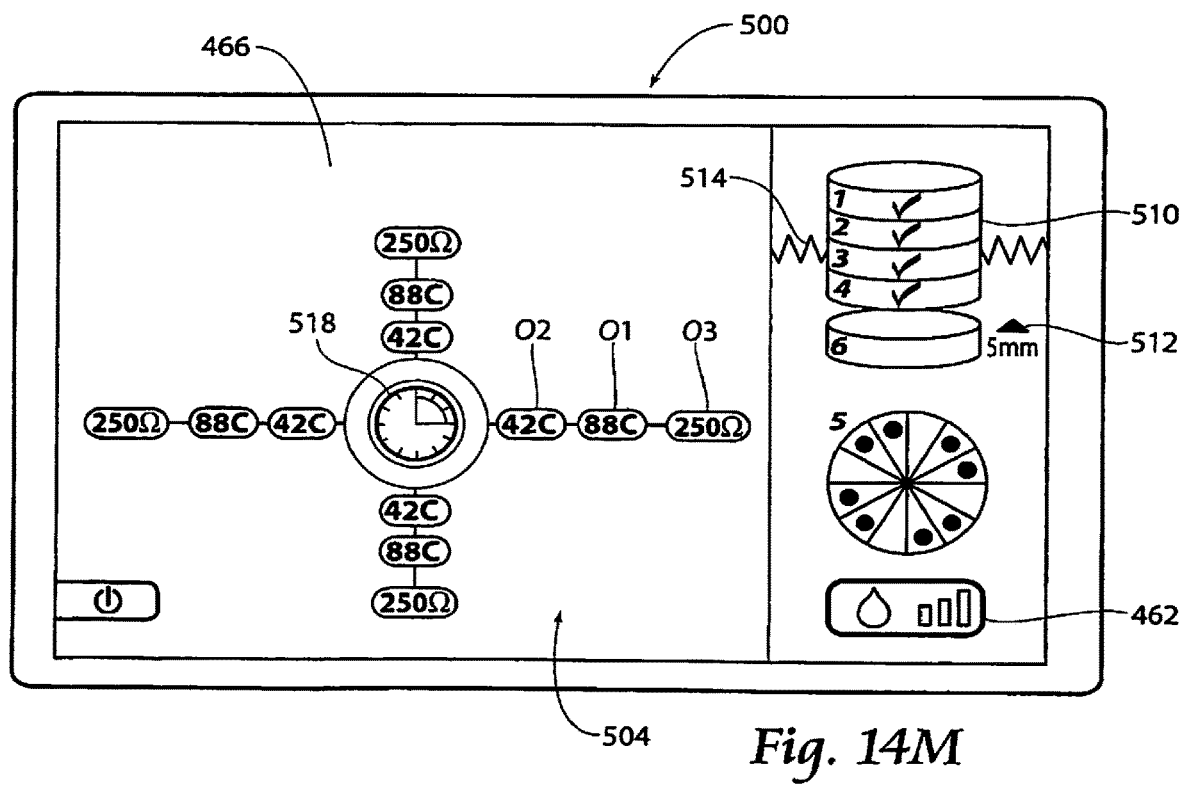
Figure 14N:
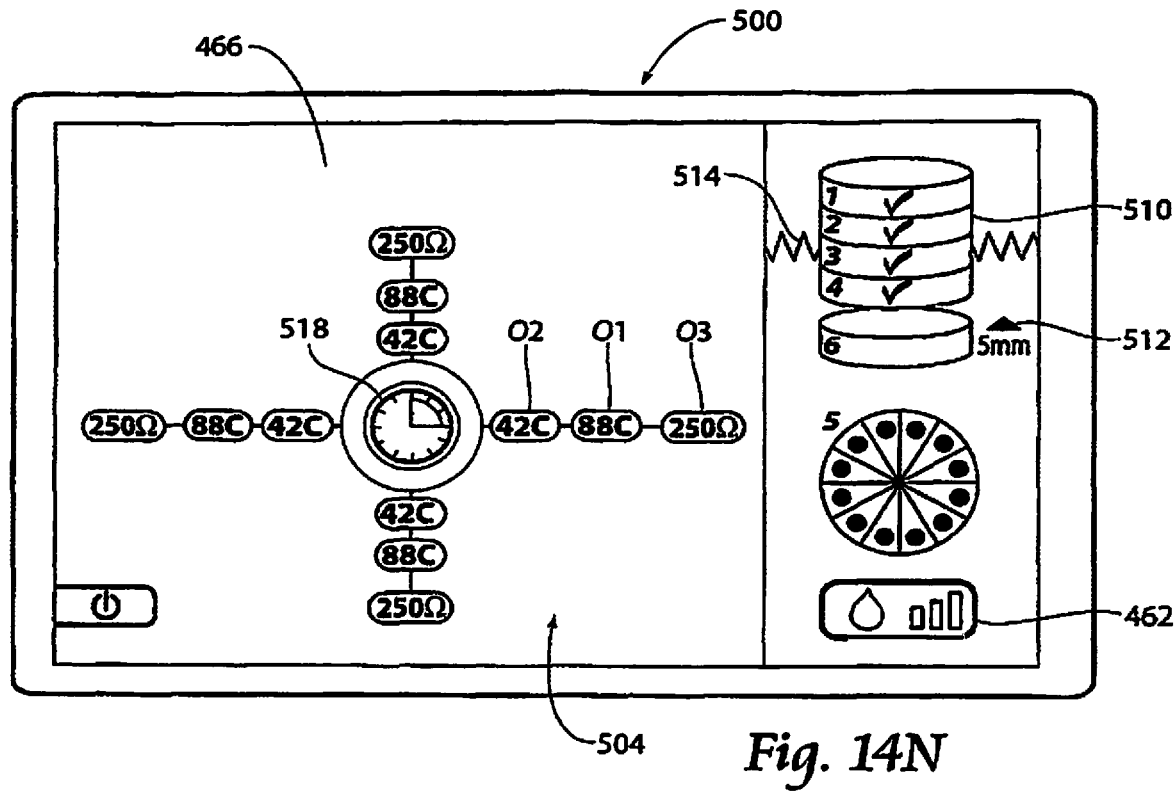

The physician proceeds to form eight lesions in Lesion Level 3 (FIGS. 14I and 14J), then moving on to Lesion Level 4 (not shown, but following the same progression as already described). All the while, the UGUI 504 visually records and confirms progress. As shown in FIG. 14K, the graphical Lesion Level cylinders for Lesion Levels 3 and 4 return edgewise when the desired number of lesions has been formed on the respective level and treatment at the level has been completed. At that time, a check mark appears on the edgewise cylinder, indicating that treatment at that level has been completed for Lesion Levels 1, 2, 3, and 4 (as shown in FIG. 14K).

As FIGS. 14K to 14N, on Lesion Levels 5 and 6, the segments in the segmented circle number twelve, indicating that twelve lesions are to be formed on these levels. In the Levels 5 and 6, there are twelve lesions circumferentially spaced 30-degrees apart (i.e., a first application of energy, followed by a 30-degree rotation of the basket 56, followed by a second application of energy, followed by a 30-degree rotation of the basket 56, followed by a third application of energy). In Level 5, the balloon structure is only partially expanded, whereas in Level 6, the balloon structure 72 is more fully expanded, to provide lesion patterns that increase in circumference according to the funnel-shaped space available in the funnel of the cardia.

Figure 14O:
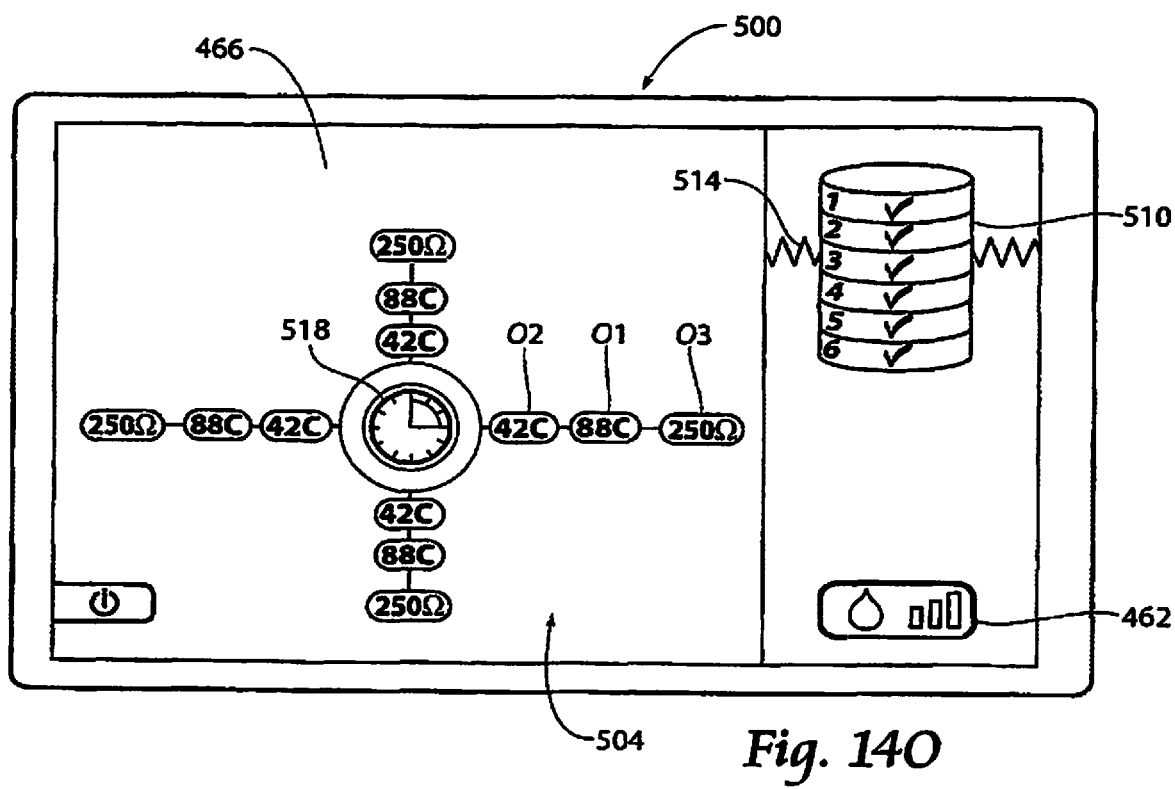

The UGUI 504 reflects completion of the treatment (see FIG. 14O).

Thus, the UGUI 504, by purposeful manipulation of different stylized graphical images, visually prompts the physician step wise to perform a process of forming a pattern of lesions comprising a plurality of axially spaced lesion levels, each lesion level comprising a plurality of circumferential spaced lesions. The UGUI 504 registers the formation of lesions as they are generated in real time, both within and between each circumferentially spaced level. The UGUI 504 therefore displays for the physician a visual record of the progress of the process from start to finish. The UGUI 504 assures that individual lesions desired within a given level are not skipped, or that a given level of lesions is not skipped.

In the UGUI 508, each Lesion Level 1 to 6 is initially depicted by a first stylized graphical image comprising an edgewise cylinder with a number identification of its level. When the formation of lesions at a given level is indicated, the UGUI 504 changes the first stylized graphical image into a second stylized graphical image, different than the first image, comprising an axial view of the cylinder, presented a segmented circle, with the numbers of segments corresponding to the number of lesions to be formed. There also appears juxtaposed with the next lesion level to be treated (still displayed as an edgewise cylinder), a marker along with a number indicating its distance from the present legion level. As the physician manipulates the device 26a to form lesions on the indicated levels, the second graphical image further changes to a third graphical image, different than the first or second images, by adding indicia within the segmented circle to reflect the formation of lesions, to guide the physician successively rotate and operate the device 26a at the lesion level. Upon forming the desired lesion pattern on a given level, the UGUI 504 again changes the third graphical image to a fourth graphical image, different than the first, second, and third graphical images, comprising an edgewise cylinder with a number identification of its level, and further an indicator (e.g. a check mark) that indicates all desired lesions have been formed at the respective level. A Marker 512 is successively updated to direct the physician to the next Lesion Level. In this way, the UGUI 504 prompts the formation of eight lesions circumferentially spaced 45-degrees apart in the Levels 1, 2, 3, and 4, and the formation of twelve lesions circumferentially spaced 30-degrees apart at Lesion Levels 5 and 6.

2. The LGUI

The LGUI 506 (FIG. 15A) generates a graphical user display that guides the physician in manipulating the device 26*b* to form a prescribed lesion pattern in the anal canal, as shown in FIG. 9. The lesion pattern comprises a plurality of axially spaced lesion levels (in the illustrated embodiment, numbered 1 to 5), each lesion level comprising a plurality of circumferential spaced lesions (in the illustrated embodiment, there are sixteen lesions, arranged in sets of four).

The display of the LGUI 506 (see FIG. 15A) shows Lesion Levels 1, 2, 3, 4, and 5, corresponding with the multiple lesion levels to be formed in the anal canal. Lesion Levels 1 to 5 are displayed as segmented discs, numbered 1 to 5, which are tilted slightly on their axes, and arranged one above the other. Each disc is divided into four quadrants.

The LGUI 506 also shows (see FIG. 15A) a dentate squiggle line 514. In preparation for the treatment, the physician visualizes in the anal canal dentate line or other desired anatomic landmark. Markers are arranged at 5 mm intervals along the barrel of the device 26*b*. Upon visualizing the dentate line, the physician notes the external marker on the barrel that corresponds to this position. With reference to the markers, the physician can then axially advance or retract the barrel in 5 mm increments, which correspond to the spacing between the lesion levels.

Next to the graphical form of the disc of Lesion Level 1 is a Guide Marker 512 (see FIG. 15A). The Guide Marker 514 indicates that formation of lesions in Lesion Level 1 is indicated. A numeric value (5 mm) is displayed in association with the edgewise cylinder of Lesion Level 1, which indicates that Lesion Level 1 is 5 mm from the anatomic landmark.

In FIG. 15A, all quadrants of the lesion level discs are unmarked. This graphical form indicates at a glance that (i) formation of lesions at Lesion Level 1 is now indicated (due to the position of the Marker 512) and (ii) no lesions have as yet been formed (by the lack of markings in the quadrants).

Figure 15B:
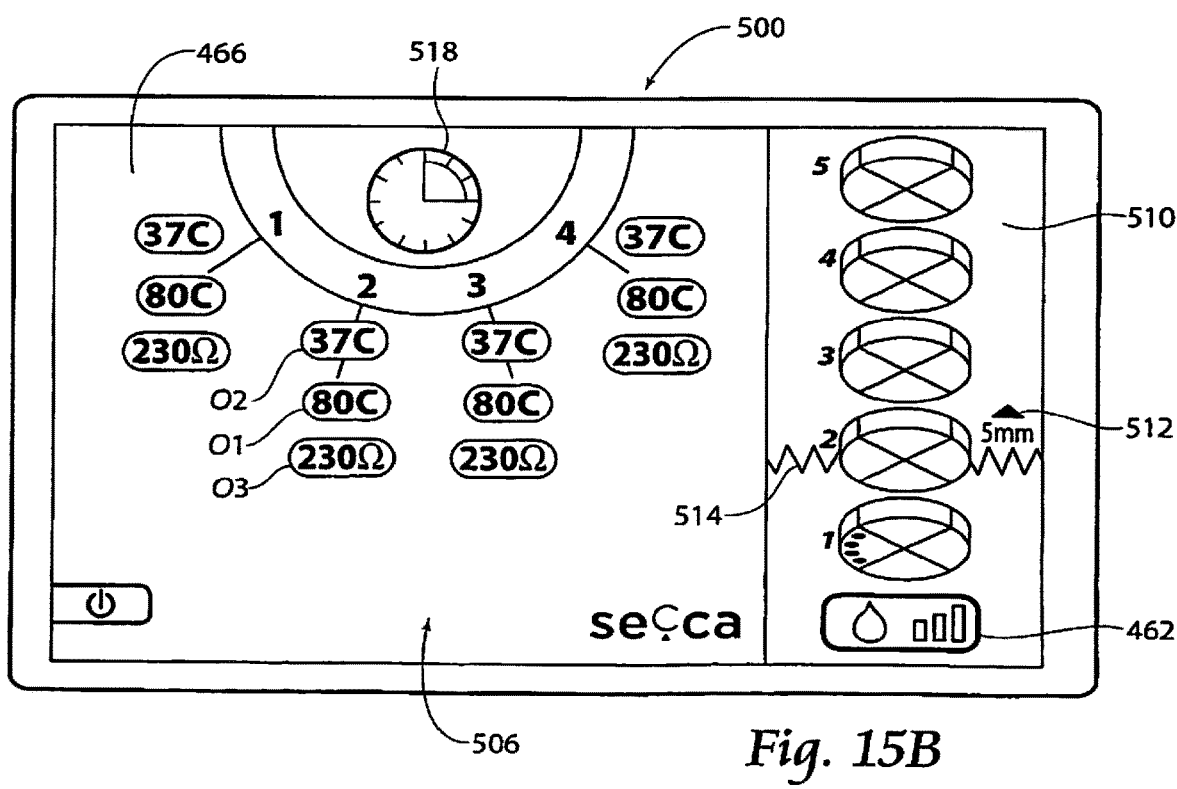

The device 26*b* includes an array of four needle electrodes arrange in an arc, which can be advanced and retracted (see FIG. 6). The array of needle electrodes is positioned at Level 1, in alignment with quadrant 1, and advanced. The physician actuates the electrodes for a first pre-set period. A Timer Icon 518 shows the application of radio frequency energy for the pre-set period. At the end of this pre-set period, treatment indicia (e.g., four dots) appear in the first quadrant of the graphical segmented discs (see FIG. 15B), indicating the formation of the first four lesions, as well as their spatial orientation in the first quadrant.

The location of the Marker 512 also changes to align with Lesion Level 2, with a numeric indicator of 5 mm. This informs the physician that after Lesion Level 1, the next lesion level will be Lesion Level 2, which is 5 mm above (superior to) Lesion Level 1.

Figure 15C:
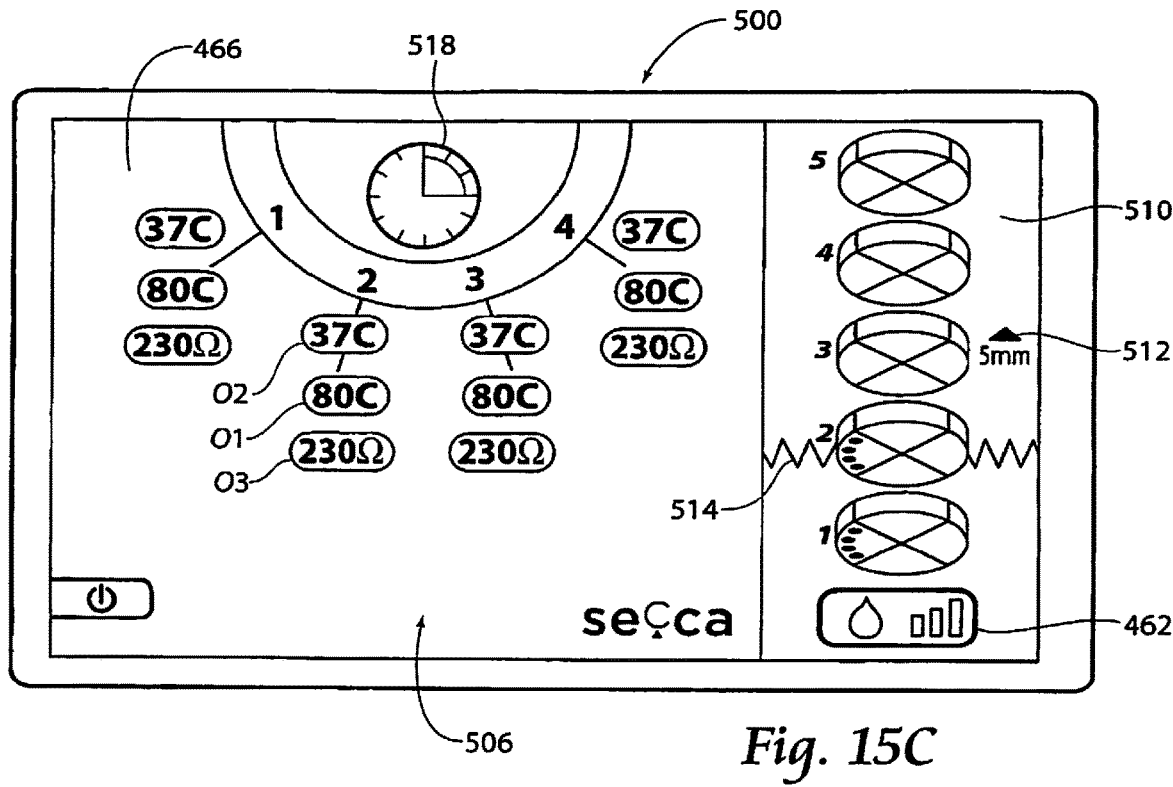

Upon the satisfactory creation of the lesion pattern in the first quadrant of Level 1, as just described, and as prompted by the Marker 512 (now aligned with Lesion Level 2), the physician actuates the button to move the needle electrodes back to their retracted positions. Still grasping the hand grip and visualizing through the viewing port, the physician moves the barrel 5 mm axially upward to Level 2, remaining rotationally aligned in the first quadrant. The physician again deploys the needle electrodes and performs another lesion generating sequence. The location of the Marker 512 also changes to align with Lesion Level 3, with a numeric indicator of 5 mm. This informs the physician that after Lesion Level 2, the next lesion level will be Lesion Level 3, which is 5 mm above (superior to) Lesion Level 2. Treatment indicia (e.g., four dots) appear in the first quadrant of the graphical segmented disc of Lesion Level 2 (see FIG. 15C), indicating the formation of the four lesions, as well as their spatial orientation in the first quadrant.

Figure 15D:
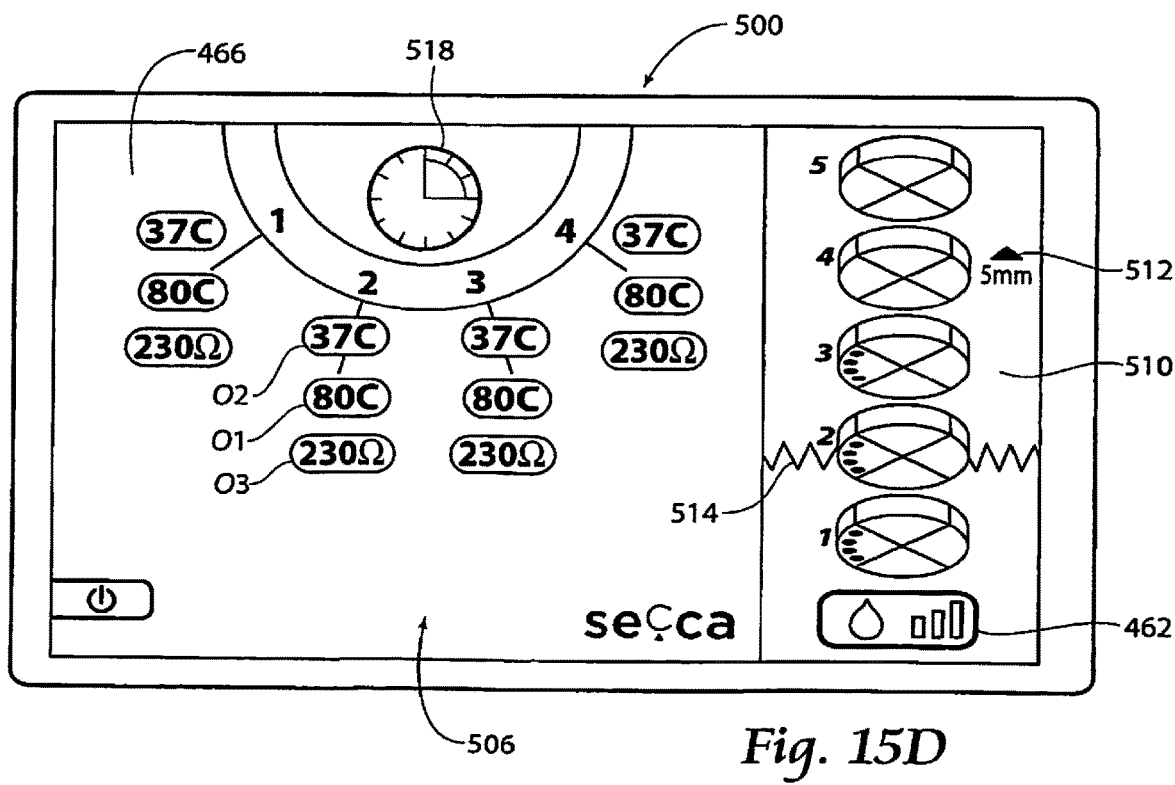
Figure 15E:
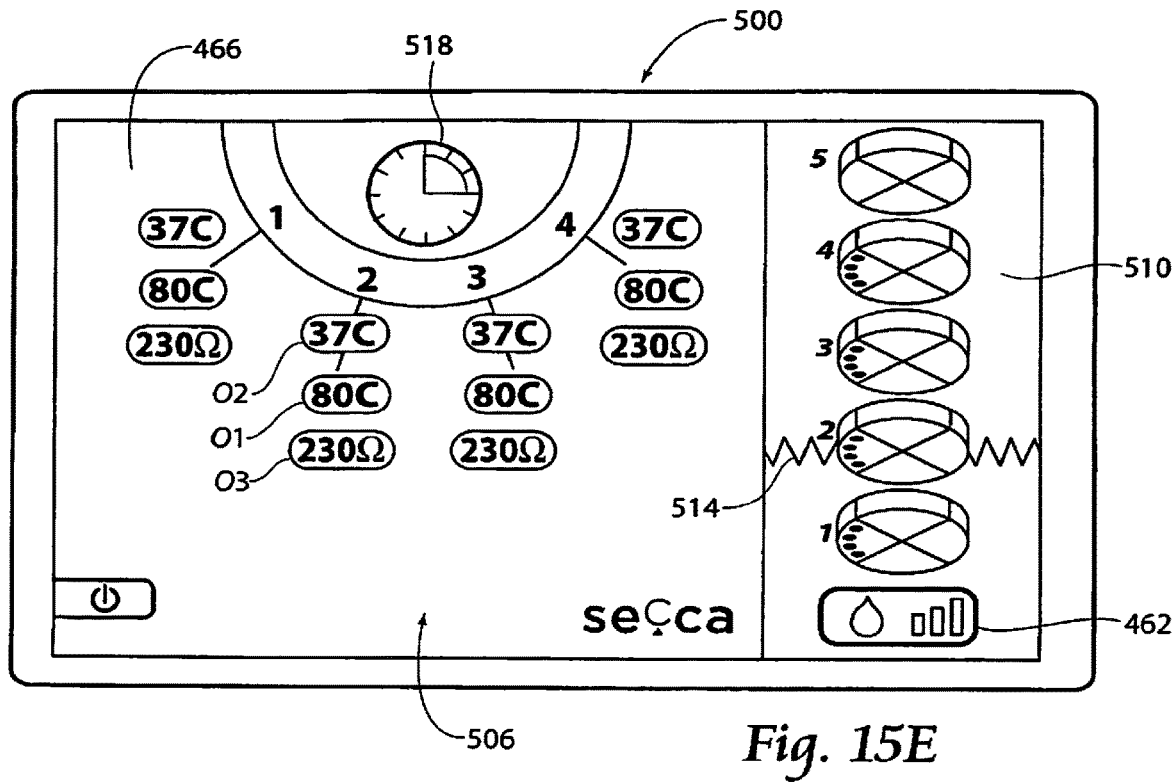
Figure 15F:
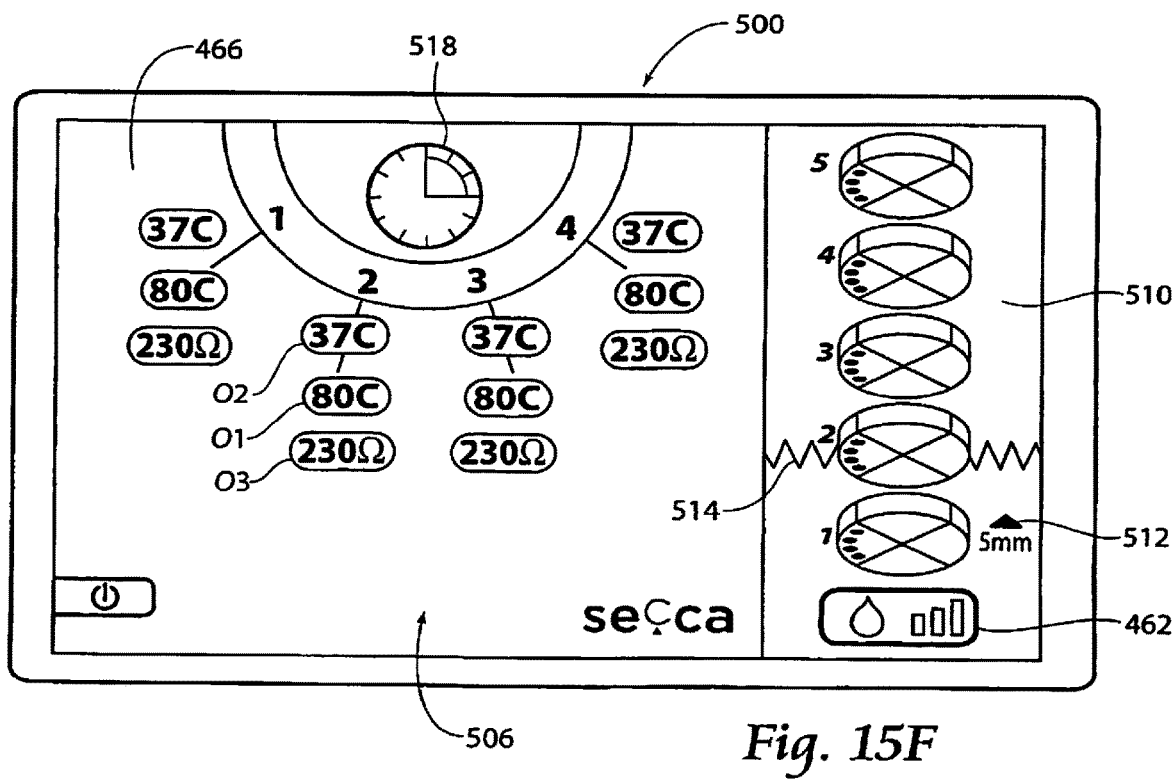

The physician repeats this sequence of steps until additional number of lesion patterns are formed within the axially spaced first quadrants in Levels 2, 3, 4, and (see FIGS. 15D, 15E, and 15F). The location of the Marker 512 also changes to align with successive Lesion Levels, to guide the physician through the lesion levels. Treatment indicia (e.g., four dots) appear in the first quadrant of the graphical segmented discs of Lesion Levels 2, 3, 4, and 5 (see FIG. 15F), indicating the formation of the four lesions, as well as their spatial orientation in the first quadrant.

Upon formation of the four lesions in quadrant 1 of Lesion Level 5, the Marker 512 returns to Lesion Level 1 (see FIG. 15F), prompting the physician to return to Lesion Level 1, and again rotate the barrel a selected arcuate distance at Lesion Level 1 into alignment with the second quadrant, i.e., by rotating the barrel by ninety degrees.

Figure 15G:
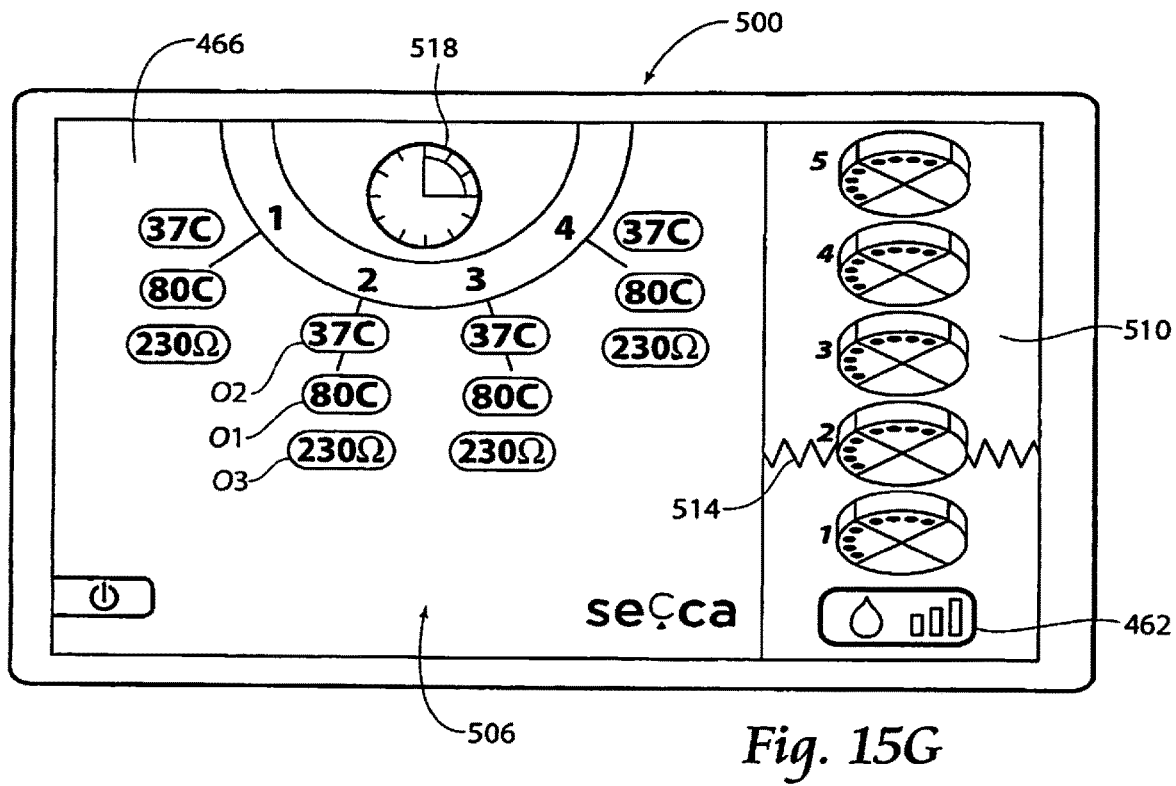

Guided by the LGUI 506, the physician again deploys the needle electrodes and performs another lesion generating sequence at quadrant 2 of Level 1. Guided by the LGUI 506 (as shown in FIG. 15G), and following the Marker 512, the physician then moves the barrel axially upward in 5 mm increments, sequentially to quadrant 2 of Lesion Level 2, then quadrant 2 of Lesion Level 3, the quadrant 2 of Lesion Level 4, and quadrant 2 of Lesion Level 5. At each Lesion Level, the physician deploys the needle electrodes and performs another lesion generating sequence at quadrant 2 of the respective level. After lesion formation at each Lesion Level, treatment indicia (e.g., four dots) appear in the second quadrant of the graphical segmented discs of Lesion Levels 2, 3, 4, and 5 (see FIG. 15G), indicating the formation of the four lesions, as well as their spatial orientation in the second quadrant.

Upon formation of the four lesions in quadrant 2 of Lesion Level 5, the Marker 512 returns to Lesion Level 1. The physician returns to Lesion Level 1, and again rotates the barrel a selected arcuate distance at Lesion Level 1 into alignment with the third quadrant, i.e., by rotating the barrel by ninety degrees.

Guided by the LGUI 506 (see FIG. 15H), the physician again deploys the needle electrodes 48 and performs another lesion generating sequence at quadrant 3 of Level 1. Treatment indicia (e.g., four dots) appear in the quadrant 3 of the graphical segmented disc of Lesion Levels 1, indicating the formation of the four lesions, as well as their spatial orientation in the third quadrant.

Figure 15H:
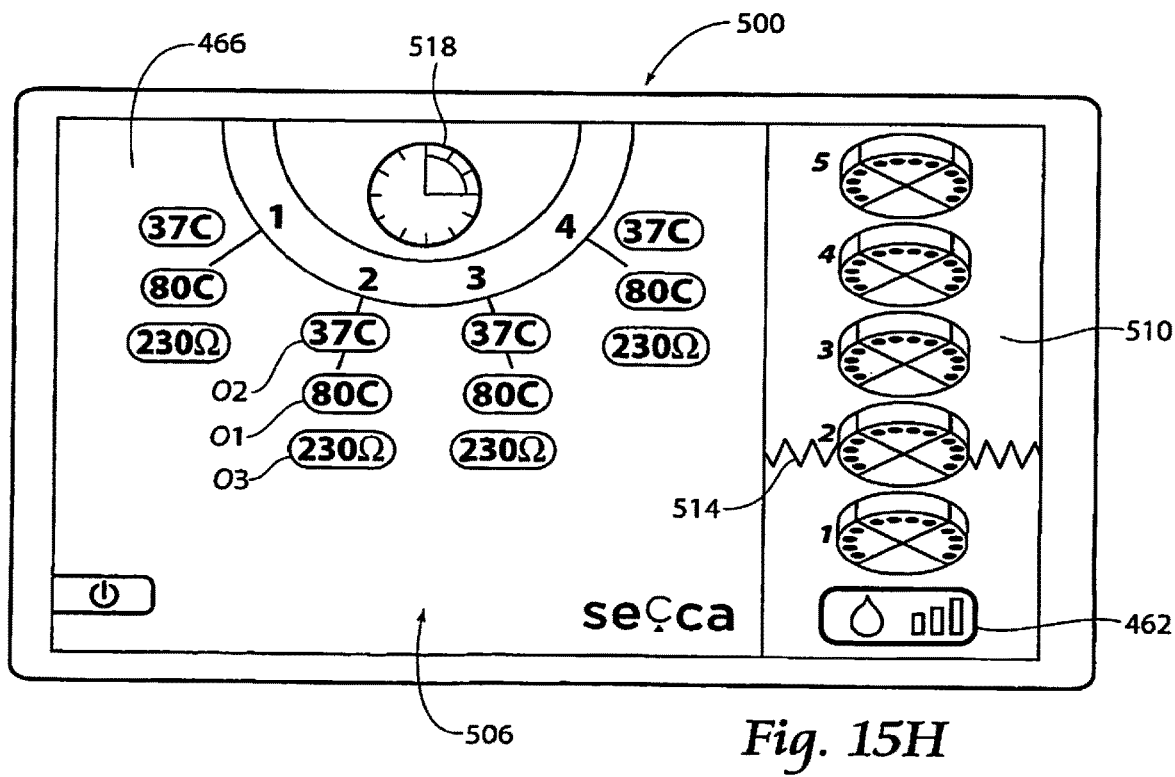

As shown in FIG. 15H, guided by the LGUI 506, and following the Marker 512 as it advances with lesion formation at each level, the physician then moves the barrel axially upward in 5 mm increments, sequentially to quadrant 3 of Lesion Level 2, then quadrant 3 of Lesion Level 3, then quadrant 3 of Lesion Level 4, and quadrant 3 of Lesion Level 5. At each Lesion Level, the physician deploys the needle electrodes and performs another lesion generating sequence at quadrant 3 of the respective level. Treatment indicia (e.g., four dots) appear in the third quadrant of the graphical segmented discs of Lesion Levels 2, 3, 4, and 5 (see FIG. 15H), indicating the formation of the four lesions, as well as their spatial orientation in the third quadrant.

Figure 15I:
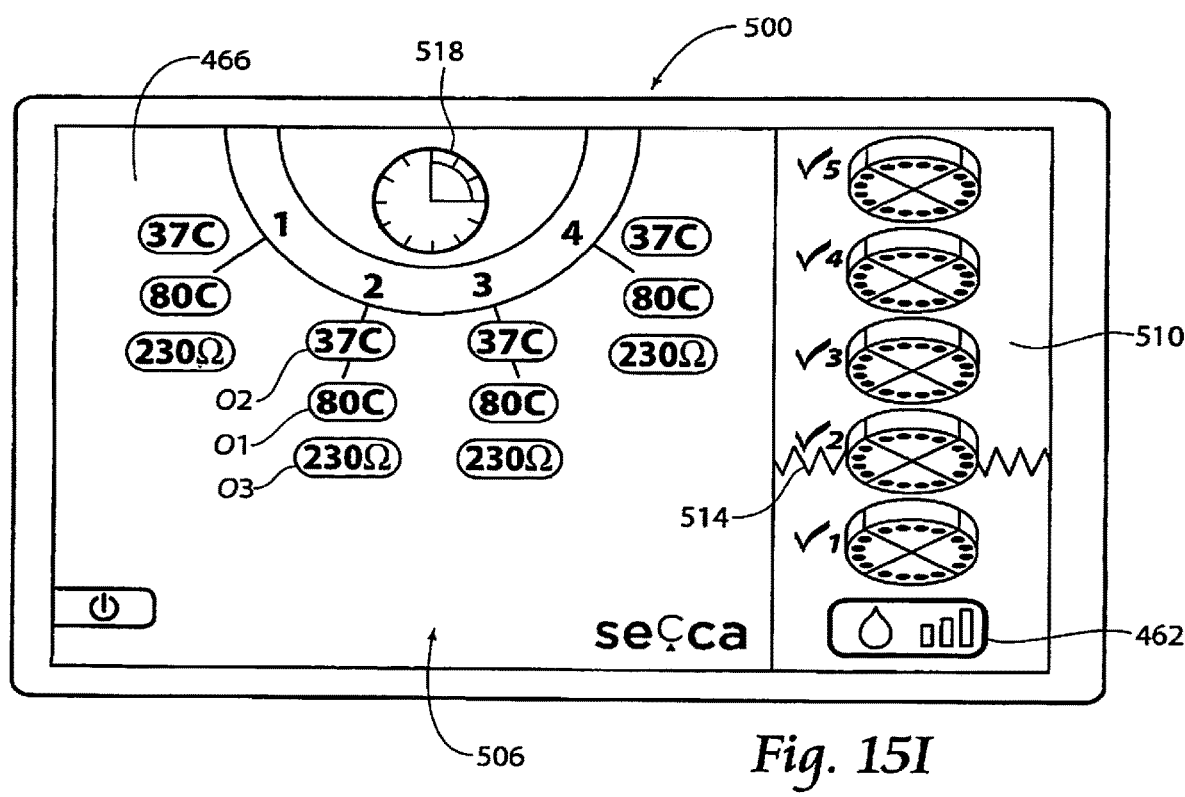

The physician repeats the above described sequence one additional time, returning the barrel to Lesion Level 1 and rotating the barrel ninety degrees into alignment with quadrant 4 of Lesion Level 1 (see FIG. 15I). The physician forms the lesion patterns quadrant 4 in the Levels 1, 2, 3, 4, and 5. Treatment indicia (e.g., four dots) appear in the fourth quadrant of the graphical segmented discs of Lesion Levels 1, 2, 3, 4, and 5 (see FIG. 15B), indicating the formation of the four lesions, as well as their spatial orientation in the second quadrant. In addition, with the formation of lesions in the fourth quadrant at each Lesion Level, the graphical disc representing the Lesion Level, each quadrant marked by four dots (indicating completion of lesion creation) is changed to additionally include an indicator, e.g., checkmark, to indicate that the respective Lesion Level has been treated (see FIG. 15I).

As described, the LGUI 506 visually prompts a user in a step-wise fashion to perform a process of forming a pattern of lesions in the anal canal comprising a plurality of axially spaced lesion levels, each lesion level comprising a plurality of circumferential spaced lesions. The LGUI 506 registers the formation of lesions as they are generated in real time, both within and between each circumferentially spaced level. The LGUI 506 displays for the user a visual record of the progress of the process from start to finish and guides the user so that individual lesions desired within a given level are all formed, and that a given level of lesions is not skipped.

Each Lesion Level 1 to 5 of the LGUI 506 is depicted by a first stylized graphical image comprising a edge-tilted disc with a number identification of its level. The discs are segmented corresponding to the regions in which lesions to be formed. There also appears juxtaposed with the next lesion level to be treated, a marker along with a number indicating its distance from the present legion level. As the physician manipulates the device 26b to form lesions on the indicated levels, the second graphical image further changes to a second graphical image, different than the first image, by adding indicia within the segmented circle to reflect the formation of lesions, to guide the physician as the device is successively operated at the lesion level. Upon forming the desired lesion pattern, the UGUI 506 again changes the second graphical image to a third graphical image, different than the first, second, and third graphical images, comprising an indicator (e.g. a check mark) indicating that all desired lesions have been format at the level. The Marker 512 is updated to direct the physician to the next Lesion Level. In this way, the UGUI 506 prompts the formation of four lesions sets of four lesions each (totaling twelve lesions) circumferentially spaced apart in the Levels 1, 2, 3, 4, and 5.

We claim:

1. A system for visually tracking on a monitor different tissue levels and different treatment regions circumferentially spaced within each tissue level of the different tissue levels for application of radiofrequency energy to a gastrointestinal tract of a patient to perform a surgical procedure, the system comprising a plurality of tissue level indicators corresponding to the different tissue levels, the different tissue levels being axially spaced and including a first, a second and a third tissue level and the tissue level indicators indicating a specific level of tissue from the first, second and third tissue levels to track which of the first, second and third axially spaced tissue levels have been treated by lesion formation and which of the first, second and third tissue levels have not been treated, each tissue level indicator of the plurality of tissue level indicators has a geometric shape subdivided into separate regions to represent the circumferentially spaced different treatment regions, wherein after treatment of each different treatment region within each of the different tissue levels, the separate region of the tissue level indicator is adapted to be visually marked as treated by a marking within the separate region to indicate lesion formation within each of the different treatment regions, wherein a first tissue level indicator of the plurality of tissue level indicators remains visible on the monitor showing lesion formation while a second tissue level indicator of the plurality of tissue level indicators is marked to indicate lesion formation in the circumferentially spaced different treatment regions in the second tissue level and while the third tissue level indicator is not yet marked to indicate lesion formation.

2. The system of claim 1, wherein the plurality of tissue level indicators are adapted to change in real time to step wise guide a user through the surgical procedure to create tissue lesions at the different tissue levels within the gastrointestinal tract, the plurality of tissue level indicators corresponding to the different tissue levels appearing on the monitor at a start of the surgical procedure.

3. The system of claim 1, wherein the plurality of tissue level indicators are adapted to change in real time to record a progress of the surgical procedure from a start to a finish of the surgical procedure, the plurality of tissue level indicators corresponding to the different tissue levels appearing on the monitor at the start of the surgical procedure.

4. The system of claim 1, wherein if an electrode channel of a radiofrequency device connected to the system is disabled, the region of the tissue level indicator of the plurality of tissue level indicators is configured to visually indicate the region of the tissue level as not treated.

5. The system of claim 1, wherein each of the plurality of tissue level indicators is disc shaped and subdivided into regions corresponding to the different treatment regions circumferentially spaced within each of the different tissue levels.

6. The system of claim 1, wherein the indicators of the plurality of tissue level indicators are adapted to visually change position on the monitor during the surgical procedure.

7. The system of claim 1, wherein each of the indicators of the plurality of tissue level indicators are adapted to visually change to a different orientation on the monitor as the corresponding tissue level is being treated.

8. The system of claim 1, wherein if an electrode channel of a radiofrequency device connected to the system is disabled, a region of the indicator of the plurality of tissue level indicators is visually indicated as not treated.

9. The system of claim 1, further comprising a temperature indicator and an electrode array indicator, the temperature indicator adjacent the electrode array indicator and spaced from the tissue level indicators configured to display a temperature reading.

10. The system of claim 1, further comprising an impedance indicator and an electrode array indicator, the impedance indicator adjacent the electrode array indicator and spaced from the tissue level indicators configured to display an impedance reading.

11. A housing comprising a radio frequency generator, a controller with an I/O device and a graphics display monitor, the graphics display monitor including a graphic display of at least a first, a second and a third indicator corresponding to a first, a second and a third axially spaced level of tissue to be treated, the first, second and third indicators simultaneously displayed and having a numeric display associated therewith for tracking in sequence the axially spaced levels of tissue to be treated, each indicator having a geometric shape divided into visual sectors to represent circumferentially spaced treatment regions within each axially spaced level of tissue, wherein a visual marking is provided within each visual sector to indicate formation of lesions in each circumferentially spaced treatment region of each axially spaced level of tissue during a surgical procedure, and a temperature indicator spaced from the visual sectors is configured to indicate temperature and an impedance indicator spaced from the visual sectors is configured to indicate impedance.

12. The housing of claim 11, wherein each indicator is disc shaped and the visual sectors are subdivisions of the disc shaped indicators to provide an indicator about a circumference within each of the levels of tissue.

13. The housing of claim 11, wherein if an electrode channel of a radiofrequency device connected to the radiofrequency generator is disabled, the visual sector of the indicator of the first, second, and third indicators is visually indicated as not treated.

14. A graphical user interface comprising a graphical display during a surgical procedure of application of radiofrequency energy to a plurality of axial levels of tissue by an electrosurgical device having a plurality of electrodes to form lesions, the graphical display adapted to provide a first visual indication of the plurality of electrodes and a second visual indication, spaced from the first visual indication, of a number and position of the lesions that are formed at the plurality of axially spaced levels of tissue and a number and position of lesions that are unformed at the plurality of axially spaced levels of tissue, the second visual indication displaying at a same time the number and position of the lesions that are formed at circumferentially spaced regions at a first level of tissue of the plurality of levels of tissue and the number and position of the lesions that are formed at circumferentially spaced regions at a second different level of tissue of the plurality of levels of tissue.

15. The graphical user of claim 14, wherein the second visual indication includes a series of indicators each corresponding to a level of tissue, the series of indicators arranged in a vertical array.

16. The graphical user of claim 14, wherein the second visual indication includes a series of indicators each corresponding to a level of tissue, and indicators of the series of indicators are adapted to visually change to a different position on the graphical display during the surgical procedure.

17. The graphical user of claim 14, wherein the second visual indication includes a series of indicators corresponding to a level of tissue and indicators of the series of indicators are adapted to visually change to a different orientation on the graphical display as the corresponding level of tissue is being treated.

* * * * *